US011890211B2

(12) United States Patent
Sanders et al.

(10) Patent No.: US 11,890,211 B2
(45) Date of Patent: *Feb. 6, 2024

(54) FIBROUS TUBULAR CONDUIT FOR STENTING APPLICATIONS

(71) Applicant: STENTIT B.V., Eindhoven (NL)

(72) Inventors: Bart Sanders, Eindhoven (NL); Maria Sol Cabrera, Eindhoven (NL); Franciscus Petrus Thomas Baaijens, Eindhoven (NL); Patricia Yvonne Wilhelmina Dankers, Helmond (NL)

(73) Assignee: STENTIT B.V., Eindhoven (NL)

( * ) Notice: Subject to any disclaimer, the term of this patent is extended or adjusted under 35 U.S.C. 154(b) by 589 days.

This patent is subject to a terminal disclaimer.

(21) Appl. No.: 17/028,119

(22) Filed: Sep. 22, 2020

(65) Prior Publication Data

US 2021/0068994 A1    Mar. 11, 2021

Related U.S. Application Data

(63) Continuation of application No. 16/068,604, filed as application No. PCT/EP2017/050317 on Jan. 9, 2017, now Pat. No. 10,813,777.

(60) Provisional application No. 62/321,842, filed on Apr. 13, 2016, provisional application No. 62/276,835, filed on Jan. 9, 2016.

(51) Int. Cl.
*A61F 2/90* (2013.01)
*A61F 2/24* (2006.01)
*A61F 2/86* (2013.01)
*A61F 2/82* (2013.01)
(Continued)

(52) U.S. Cl.
CPC .............. *A61F 2/90* (2013.01); *A61F 2/2418* (2013.01); *A61F 2/82* (2013.01); *A61F 2/86* (2013.01); *A61F 2/958* (2013.01); *A61F 2210/0004* (2013.01); *A61F 2240/001* (2013.01);
(Continued)

(58) Field of Classification Search
CPC ...... A61F 2/82; A61F 2/86; A61F 2/90; A61F 2/2418; D01D 5/0007; D01D 5/0038; D01D 5/0046
See application file for complete search history.

(56) References Cited

U.S. PATENT DOCUMENTS 6,689,160 B1    2/2004  Okuda et al.
7,824,601 B1   11/2010  Stankus et al.
(Continued)

FOREIGN PATENT DOCUMENTS

EP    0894505    2/1999
EP    1308180    5/2003
(Continued)

OTHER PUBLICATIONS

International Search Report, International Patent Application No. PCT/EP2017/050317, dated Mar. 23, 2017.

*Primary Examiner* — Brian A Dukert
(74) *Attorney, Agent, or Firm* — McCoy Russell LLP

(57) ABSTRACT

A stent composed by a bioabsorbable network of polymer fibers that can be rearranged upon expansion, accommodating for diameter enlargement without the need of a strut or strut pattern and providing temporary support to a biological duct, is provided. Additionally, a stent is provided where the rearranged fibrous network of its expanded state can act as a scaffold for cell infiltration and promote autologous tissue formation.

19 Claims, 23 Drawing Sheets

A: Random Fiber Orientation

State 1

State 2

(51) Int. Cl.
*A61F 2/958* (2013.01)
*D01D 5/00* (2006.01)

(52) U.S. Cl.
CPC ...... *A61F 2250/0067* (2013.01); *D01D 5/003* (2013.01); *D10B 2509/06* (2013.01)

(56) References Cited

U.S. PATENT DOCUMENTS

| | | | | |
|---|---|---|---|---|
| 8,048,150 B2* | 11/2011 | Weber | | A61F 2/07 |
| | | | | 623/1.42 |
| 8,142,501 B2* | 3/2012 | Macossay-Torres | | |
| | | | | D01D 5/0007 |
| | | | | 623/13.2 |
| 10,842,611 B2* | 11/2020 | Thian | | A61F 2/0077 |
| 2014/0172074 A1* | 6/2014 | Concagh | | A61F 2/90 |
| | | | | 623/1.2 |

FOREIGN PATENT DOCUMENTS

| | | |
|---|---|---|
| EP | 2228081 | 9/2010 |
| JP | 2005-168757 | 6/2005 |
| WO | 2008/154608 | 12/2008 |

\* cited by examiner

A: Random Fiber Orientation
*State 1*
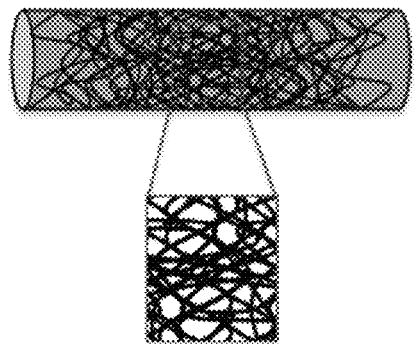
*State 2*
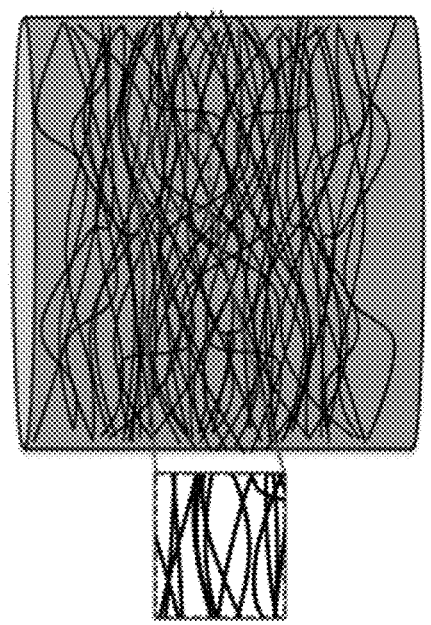
FIG. 4A

B: Controlled Fiber Orientation
State 1
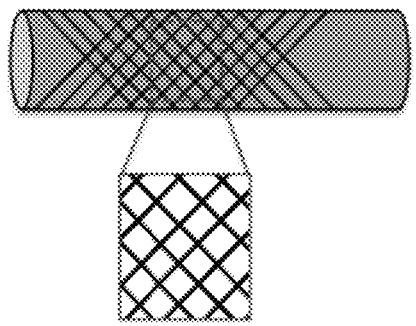
State 2
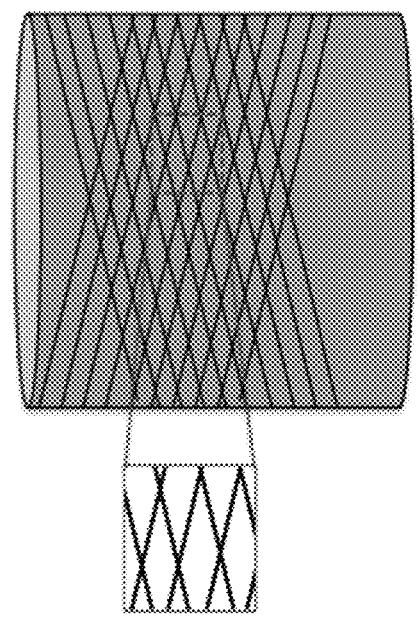
FIG. 4B

B: Controlled Fiber Orientation
State 1
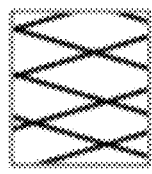
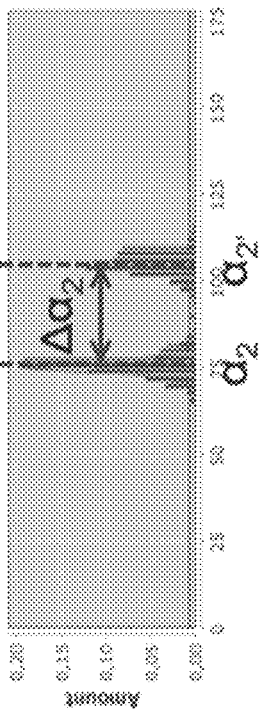
Main angle: $\alpha_1 = 42.84°$ & $\alpha_{1'} = 137.16°$
$\boxed{\Delta\alpha_1 = 94.32°}$
Dispersion: $\sigma_1 = 2.62°$ & $\sigma_{1'} = 2.13°$
Two peaks before stretch
Main parameter is:
$$I_{\Delta\alpha} = \frac{\Delta\alpha_2}{\Delta\alpha_1}$$
State 2
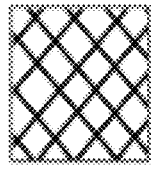
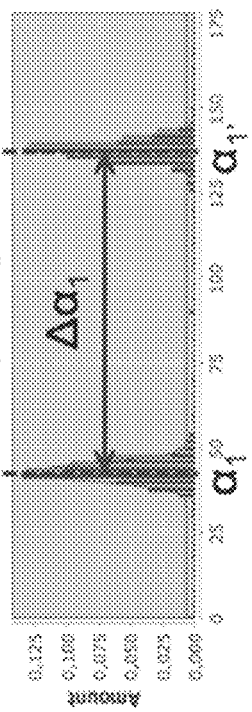
Main angle: $\alpha_2 = 75.45°$ & $\alpha_{2'} = 104.55°$
$\boxed{\Delta\alpha_2 = 29.10°}$
Dispersion: $\sigma_2 = 1.63°$ & $\sigma_{2'} = 1.80°$
FIG. 5B

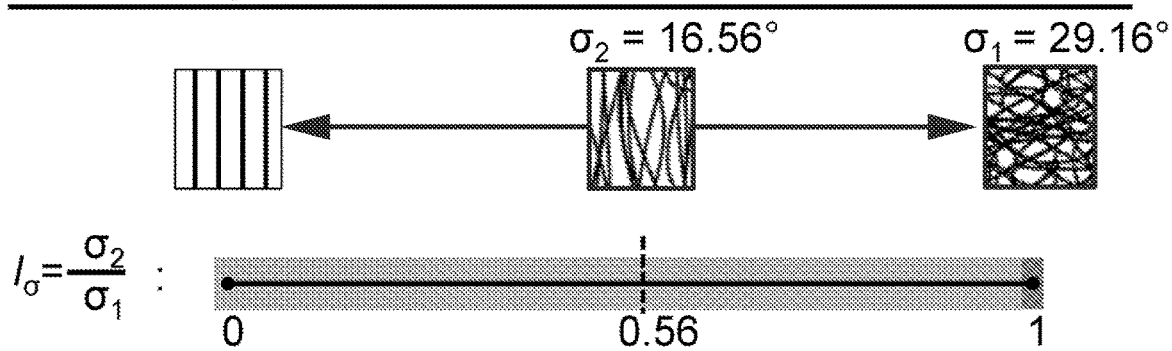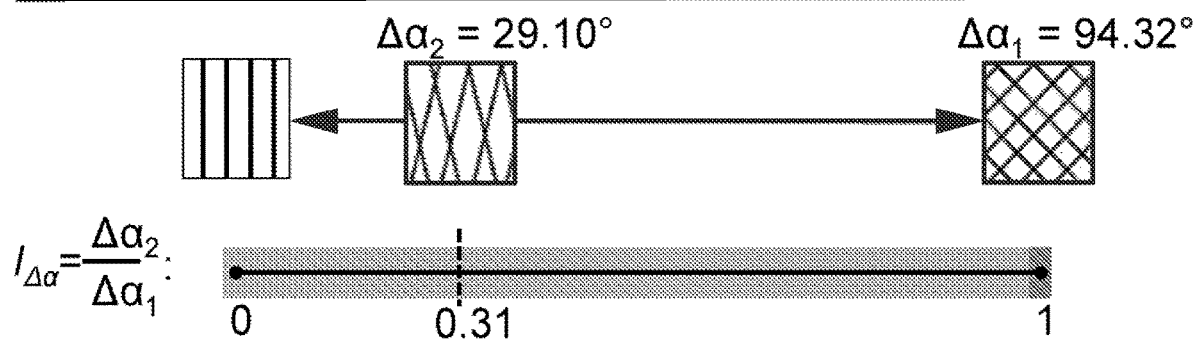
FIG. 6

FIGs. 7A-F

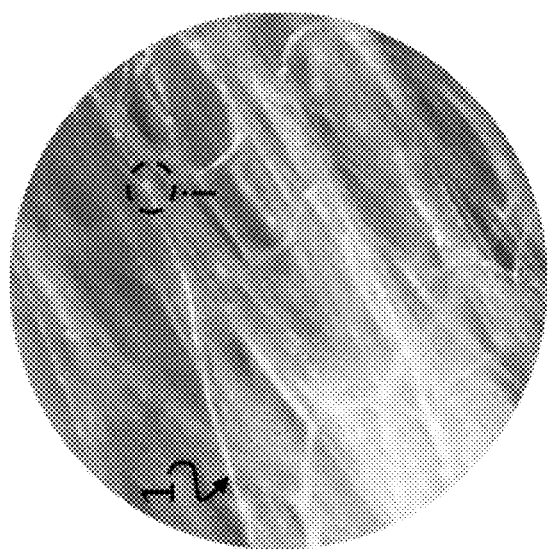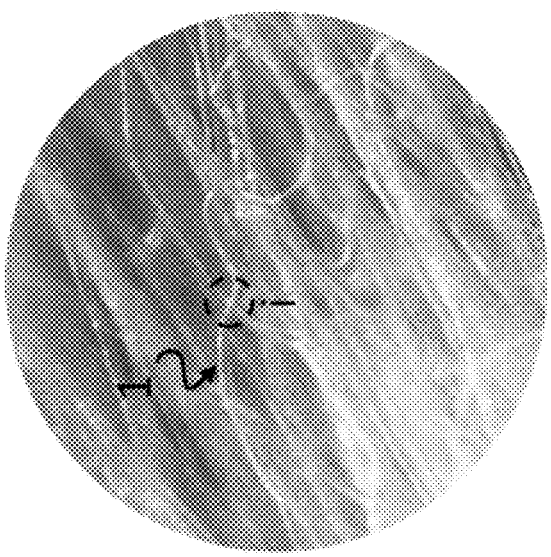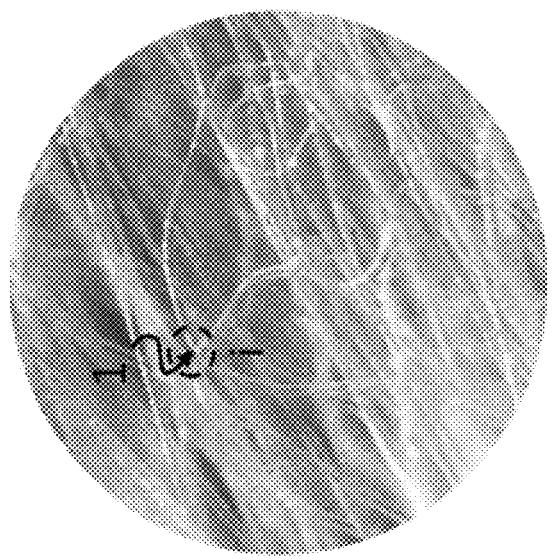
FIG. 15

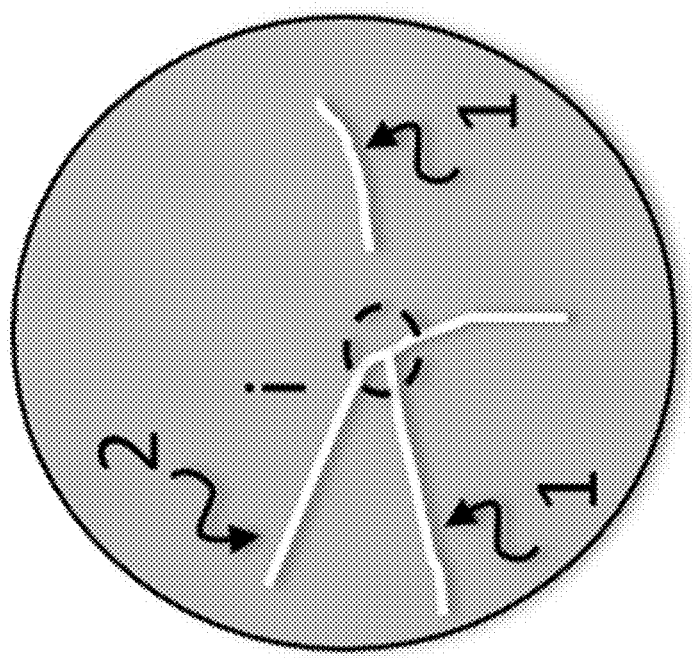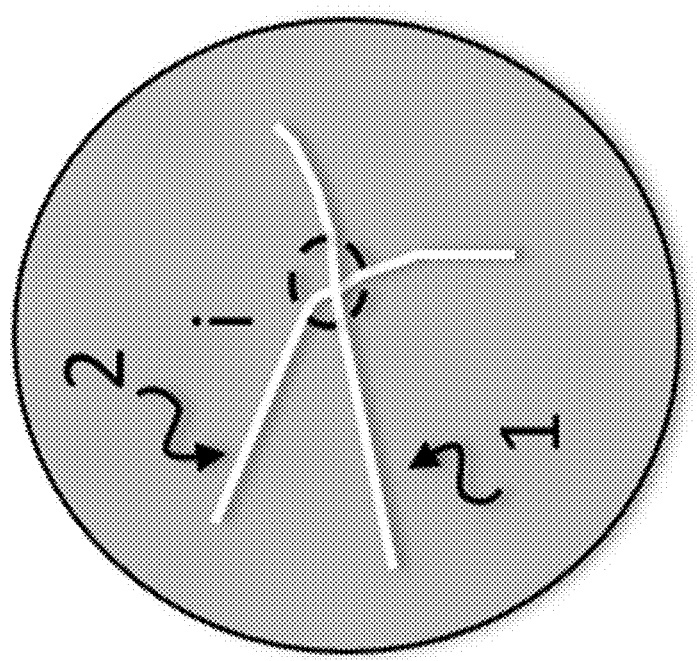
FIG. 17

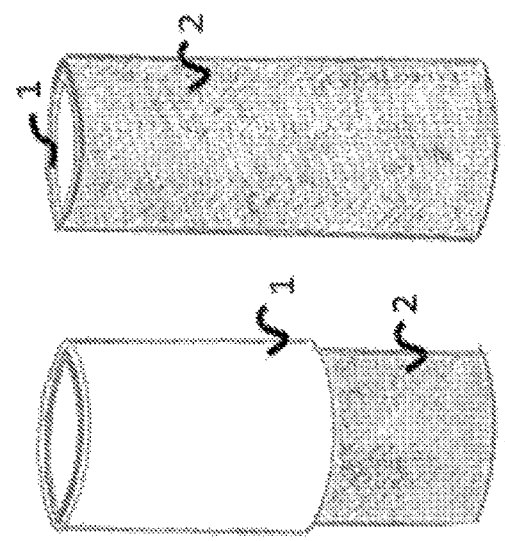
FIG. 20B
FIG. 20C
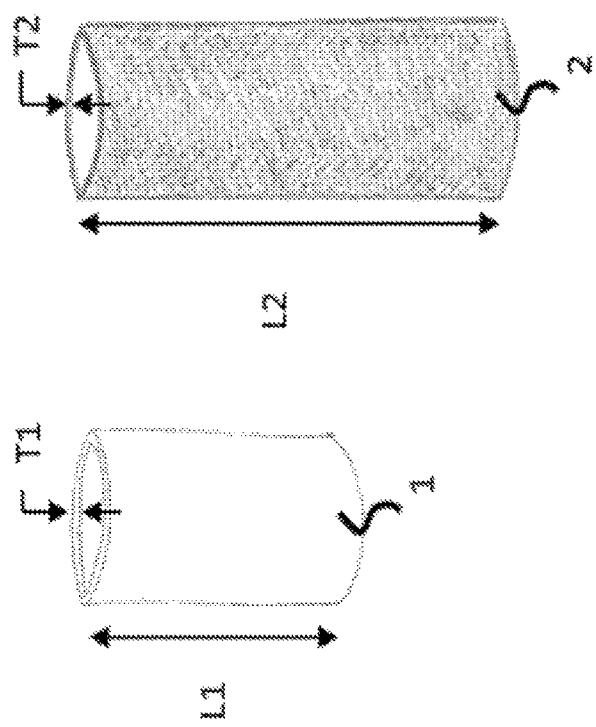
FIG. 20A
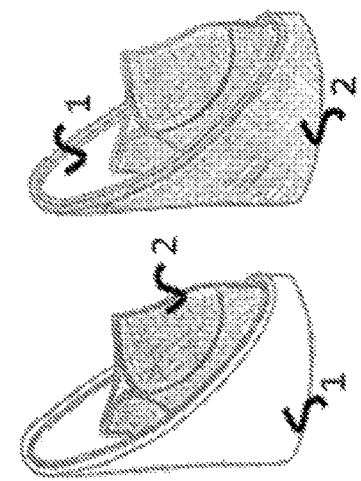
FIG. 20E
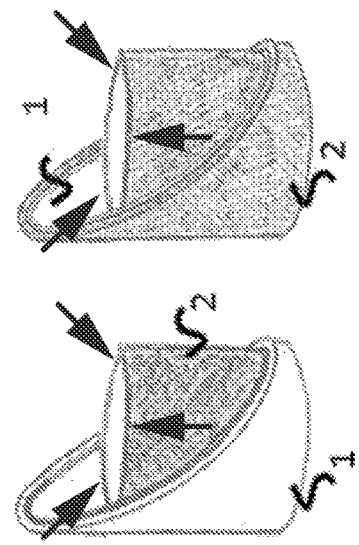
FIG. 20D

FIBROUS TUBULAR CONDUIT FOR STENTING APPLICATIONS

CROSS-REFERENCE TO RELATED APPLICATIONS

This application is a continuation of U.S. patent application Ser. No. 16/068,604, filed Jul. 6, 2018, which is a Section 371 U.S. national stage entry of International Patent Application No. PCT/EP2017/050317, filed Jan. 9, 2017, which claims priority to expired U.S. Provisional Patent Application No. 62/321,842, filed Apr. 13, 2016 and expired U.S. Provisional Patent Application No. 62/276,835, filed Jan. 9, 2016, the contents of which are hereby incorporated by reference in their entireties.

FIELD OF THE INVENTION

The invention relates to stents and regenerative medicine. In particular, the invention relates to fibrous tubular conduits with stenting capacity upon expansion that serve as minimally-invasively deliverable scaffolds for cell infiltration and trigger tissue production using the patient's own cells.

BACKGROUND OF THE INVENTION

Stents are generally defined as a tubular network of structural elements usually called struts or bar arms, where expansion is described as a movement of the individual structural elements. Methods to create a strut pattern on tubular structures include laser cutting, die punching, chemical etching, etc. Upon expansion, the stent struts move away from each other giving raise to diameter enlargement. Balloon-expandable and self-expanding stents rely on the presence of struts to be deployed minimally-invasively and on the mechanical properties of the base material to withstand the forces exerted by the implantation tools and the host tissue.

Technological advances in the field of regenerative medicine have shown that fibrous grafts can induce autologous tissue formation. Tubular fibrous structures made out of bioabsorbable polymers can be implanted to act as temporary scaffolds that guide tissue formation. However, grafts with regenerative capacity cannot act as a stent. Due to their lack of support capability, they require a surgical intervention or must be combined with an additional support device such as a stent to be implanted.

Bioabsorbable polymers with high mechanical properties such as PLA have the downside of exhibiting brittle fracture. Fibers made out of brittle polymers exhibit low deformation before they reach their breaking point. Nevertheless, wavy fibers made out of the same material may first straighten and ultimately stretch and deform, first elastically and later on plastically. Furthermore, the presence of interconnections within these fibers will result in the possibility of overcoming these interconnections upon stretching. A tubular construct made out of an interconnected network of fibers allows to benefit from the described mechanisms to achieve expansion of the construct without compromising its integrity and providing the capacity to fulfill a structural function upon expansion.

The present invention advances the art by overcoming at least some of the current shortcomings towards a support device that can be deployed, without the use of a strut pattern, by rearrangement of the fibrous network. Additionally the present invention advances the art by providing this support device with the capacity to promote autologous tissue formation, acting as a regenerative stent.

SUMMARY OF THE INVENTION

The present invention provides a biocompatible, bioresorbable stent. The stent is a tubular construct composed of a network of fibers that are able to rearrange to provide diameter enlargement at the implantation site without relying on a strut pattern. Furthermore, the tubular construct in its expanded configuration is able to provide structural support to the host tissue, allowing minimally-invasive anchoring, and serves as a scaffold with regeneration, restoration, growth and/or repair capabilities, enabling cell infiltration/adhesion/proliferation and new tissue formation if required.

The term "fibrous network" makes reference to an arrangement of interconnected fibers, where the fibers take the form of filament threads and two types of interconnections can be defined. Fibers can lie adjacent or on top of each other, defined as non-bonded interconnected fibers. Fibers can be merged while lying adjacent or on top of each other, defined as physically-bonded interconnected fibers.

The fibrous tubular network is able to act as a stent in the sense that it can provide structural support to a biological duct after minimally-invasive implantation, but differs from other stents by not relying on macroscopic voids, defined by the contours of the stent struts, to accommodate for diameter expansion, but instead fully relies on rearrangement of its fibrous network.

The stent differs from other vascular grafts as it provides the possibility of minimally-invasive implantation without requiring an additional medical device (i.e. complementary stent) to provide structural support to the graft and/or enable anchoring of the graft within the host tissue, preventing migration.

The invention is both a stent and a tissue-engineering scaffold at the same time, defining a fibrous bioresorbable stent with regenerative capacity, or in short defined as a regenerative stent.

Specifically, a stent is provided for implantation into a biological duct. The stent is an expandable tubular construct made out of a fibrous network. The fibrous network distinguishes a first state with a first diameter of the tubular conduit determined by a first fiber orientation. The first fiber orientation is characterized by a first fiber dispersion and a first main angle difference, and a first average fiber diameter. The fibrous network further distinguishes a second state with a second diameter of the tubular conduit determined by a second fiber orientation. The second fiber orientation is characterized by a second fiber dispersion and a second main angle difference, and a second average fiber diameter. The first diameter of the tubular conduit is smaller than the second diameter of the tubular conduit.

The transition from the first state to the second state is accommodated only by rearrangement of the fibers in the fibrous network and does not rely on a strut pattern. The rearrangement of the fibrous network from the first state to the second state is accomplished by: (i) stretching the fibers in the fibrous network, (ii) by sliding, breaking, or a combination thereof of the fiber interconnections in the fibrous network, and can be facilitated by acting on the wettability of the fibrous network, or a combination of (i) and (ii).

The fibrous network in the second state provides mechanical support to the biological duct. The fibrous network in the second state may allow for cell infiltration and act as a scaffold to induce autologous tissue formation.

In one variation, the first fiber orientation is an arrangement of random fibers, and in this arrangement the first fiber dispersion is larger than the second fiber dispersion.

In another variation, the first fiber orientation is an arrangement of controlled fibers and in this arrangement the first main angle difference is equal or larger than the second main angle difference.

In yet another variation, the first fiber diameter is equal to or larger than the second fiber diameter.

In still another variation, the rearrangement of the fibrous network can be facilitated by acting on the wettability of the fibrous network to accommodate the transition from state 1 to state 2.

In still another variation, the tubular construct can be composed of one or more layers.

In still another variation, the tubular construct is shaped to induce changes in geometry or openings.

In another embodiment, the invention pertains to a method for manufacturing a stent with bio-absorbable fibers including the steps of providing a tubular mold, defining a fibrous polymer network on the mold, and separating the material from the mold. The fibrous network can be, but is not necessarily, produced by electrospinning.

In yet another embodiment, the invention pertains to a method of manufacturing a valved-stent including the steps of providing a leaflet structure to the stent (either by suturing the leaflets, shaping or defining leaflets by a less dense fibrous network that can be bent inwards).

In still another embodiment, the invention pertains to a method for minimally-invasive relief of obstructive disease, including identifying an obstructed blood vessel or other tubular conduit in need, and inserting a tubular construct into said vessel or conduit. The composition can, but not necessarily, allow for new tissue formation.

In still another embodiment, the invention pertains to a method for minimally-invasive delivery of tissue-engineering scaffolds for blood vessels, including identifying a blood vessel in need of tissue repair or engineering, and inserting the tubular construct into the blood vessel. The new passage for blood is engineered inside the native artery.

In still another embodiment, the invention pertains to a method of minimally-invasive treatment of a patient with a cardiovascular disease, including identifying a blood vessel in a patient in need of obstruction relief or tissue engineering, and inserting the a tubular construct into the blood vessel.

In still another embodiment, the invention pertains to a method of minimally-invasive treatment of aneurysmatic arteries, including identifying a blood vessel with an aneurysm, and inserting a tubular construct into the blood vessel. The new passage for blood is engineered within the native artery In still another embodiment, the invention pertains to a method of minimally-invasive treatment of congenital heart disease in growing patients, including identifying a blood vessel in said patients, and inserting a tubular construct into the blood vessel. The new passage for blood is engineered within the native artery and does not hamper somatic growth.

BRIEF DESCRIPTION OF THE DRAWINGS

FIGS. 4A-B show according to an exemplary embodiment of the invention how the fibers will reorganize in a random fiber orientation scenario for a construct going from state 1 to an enlarged diameter in state 2 (FIG. 4A), and how the fibers will reorganize in a controlled fiber orientation scenario for a construct going from state 1 to an enlarged diameter in state 2 (FIG. 4B).

FIGS. 5A-B show according to an exemplary embodiment of the invention after image analysis on the microscopically obtained images, how the main angle and dispersion of the constructs alter when going from state 1 to state 2 in a random fiber orientation scenario. Here the main parameter of interest is the realignment index, $I_\sigma$ (FIG. 5A). In case of the controlled fiber orientation scenario, two clear peaks can be identified after image analyses processing, where in this case the main parameter of interest is the reorientation index, $I_{A\alpha}$ (FIG. 5B).

FIG. 6 shows according to an exemplary embodiment of the invention the range of the realignment ($I_\sigma$) and reorientation ($I_{A\alpha}$) index, which would be applicable for making the transition from state 1 to state 2 (FIG. 6).

FIG. 14B shows the device undergoing the transition from state 1 to state 2 upon stent deployment, by which the device is anchored into the artery. FIG. 14C shows, after removal of the balloon catheter, that the device maintains mechanical support to keep the stenotic area open. FIG. 14D shows a magnification of the wall of the construct, to reveal the porous structure being entirely composed of layers of stacked fibers composing a fibrous network. FIG. 14E shows, the ability for host cells to infiltrate the porous mesh. In the example, cells from the bloodstream simultaneously adhere to the fibers inside the as well as to the fibers on the luminal side simultaneously. FIG. 14F shows the fibrous network being resorbed by the body, as the cells synthesize new tissue filling up the voids inside the fibrous mesh.

FIG. 15 shows according to an exemplary embodiment of the invention a sliding non-bonded interconnection (i) initially located at reference point 1 and relocated upon expansion of the construct

FIG. 17 shows according to an exemplary embodiment of the invention partial break of interconnection i of physically bonded fibers 1 and 2, disrupting one of the fibers, i.e. fiber 1.

FIG. 18A also shows that the stent provides structural support to the artery after implantation by displaying a patent and opened artery. FIG. 18B shows histology on the explant of the embodiment two weeks after implantation in the abdominal aorta of a rat. Cells are present in both the native artery as well as on the stent. Uniform infiltration of host derived cells is marked by the highlighted dots representing individual cells. In FIG. 18C a histology picture shows a section of the stent inside the abdominal aorta of a rat. The native artery is shown on the top right, where the embodiment is on the bottom left. Signs of new tissue formation throughout the stent, already two weeks after implantation, is evidenced by the presence of dark stained tissue components.

FIGS. 20A-E show according to an exemplary embodiment of the invention a method to produce a valved-stent. The valved-stent has a fibrous polymer tubular conduit (1), of thickness T1 and length L1 that acts as a stent (FIG. 20A) and a fibrous polymer tube (2) of thickness T2 and length L1 that acts as a valve scaffold (FIG. 20B). The valve scaffold can be placed inside or outside the stent (FIG. 20C). The valve scaffold is flipped inwards to create the valve inside the stent (FIG. 20D). Constraints, such as bioabsorbable sutures, or inserts can be placed on the scaffold, defining the leaflets of the valve (FIG. 20E). In this case, a tri-leaflet valved-stentis created.

DETAILED DESCRIPTION

The term "tubular" pertains to an approximate shape of a cylinder and can include conical shapes or other variations such as curvatures, side branches, bifurcations, sinuses, ovality, concave and convex shaped segments.

The term "biological duct" refers to a part of the circulatory system including cardiovascular system (pulmonary and systemic circulation, i.e. vasculature related to the heart such as the coronary vessels as well as the peripheral vasculature), neurovascular system, and lymphatic system, related to arteries, veins and capillaries, part of the digestive system (including the gastrointestinal tract), part of the urinary system, or any related organ thereof, or any other part of a biological system where a duct can be defined and the duct is suitable to receive the stent according to embodiments of the present invention.

The term "structural support" refers to the capacity to open a biological duct causing an increase in diameter or maintaining the original diameter of the biological duct after recoil, preventing collapse and or maintaining patency. One way to evaluate the structural support capacity is to determine the force after vertical or radial compression.

The term "scaffold" refers to a structure that enables to infiltrate, attach and/or grow cells and/or tissue.

The term "stent" refers to a structure that provides structural support to the biological duct upon self-expansion or balloon expansion.

The term "construct" refers to a tubular shape that can act as scaffold or a stent. For example, a scaffold can be defined as a construct that does not necessarily provide structural support.

The term "regenerative stent" refers to a tubular fibrous construct that acts as a scaffold and a stent simultaneously.

Figures 1A, 1B, 1C:
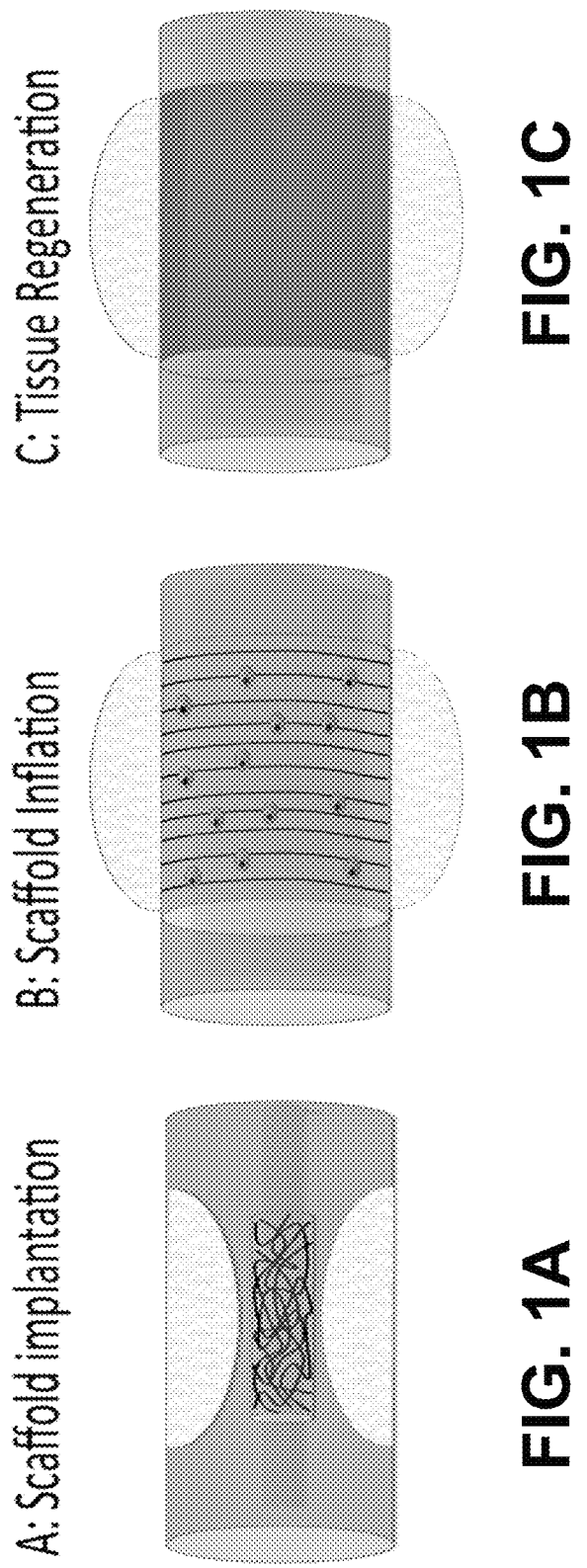
FIGS. 1A-C show according to an exemplary embodiment of the invention implantation of the construct inside an obstructed vessel (FIG. 1A), the construct expands, fibers reorganize and cells from the blood infiltrate the fibrous mesh (FIG. 1B), where cells synthesize new tissue while the fibers safely dissolve over time where after a newly formed vessel remains (FIG. 1C).
Figure 14:
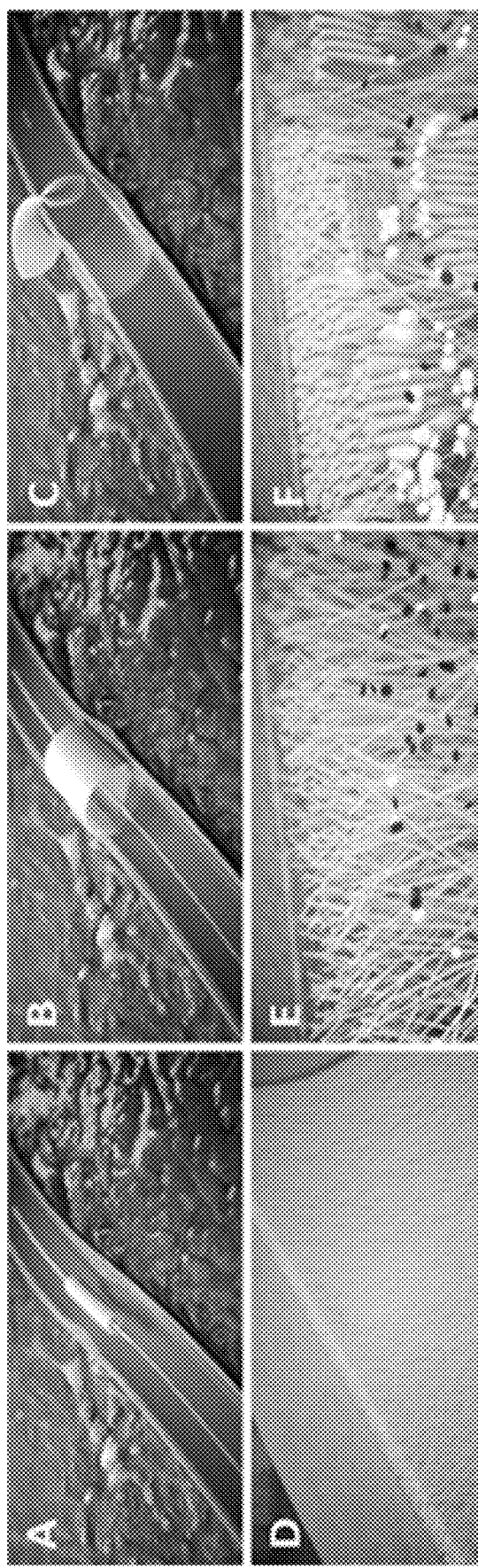
FIGS. 14A-F show according to an exemplary embodiment of the invention in FIG. 14A the device being inserted using a minimally-invasive approach mounted on a balloon catheter.

This invention describes a tubular construct, composed of a bioabsorbable fibrous network having layers of interconnected fibers. The construct can be minimally-invasively delivered into a biological duct. Once at the intervention location (FIG. 1A), the construct will undergo the transition from state 1 (FIG. 14A) to state 2 (FIG. 14B), inducing fibers to enhance rearrangement towards the circumferential direction (FIG. 2) upon expansion, enabling diameter enlargement of the construct. The construct can provide structural support to the biological duct in state 2 acting as a stent that does not rely on a strut pattern to enable expansion (FIG. 14C). Because of its fibrous nature, pores are defined within the structure (FIG. 14D) and cells from the blood and adjacent tissue can infiltrate the construct (FIG. 1B & FIG. 14E). The infiltrated cells can synthesize new tissue (FIG. 14F). Over time, the fibrous network can safely dissolve inside the body. This will eventually result in reconstructed tissue (FIG. 1C). The additional benefit for cardiovascular applications is that, due to the consistent porous structure, a gradual and uniform degradation of the construct can be expected and endothelialization will be eased, reducing the risk of inflammation and thrombus formation. Furthermore, due to the lack of a strut pattern in the stent profile, severe turbulent flow is expected to be prevented.

By combining the advantages of a fully biodegradable stent composed of a fibrous network, together with the advantages of a regenerative scaffold, this device could allow for: minimally-invasive delivery, large expansion ratios, structural support upon inflation, temporary support, enhanced resorption, internal leakage prevention, full lesion coverage, cell infiltration, natural tissue formation, construct foreshortening prevention, uniform endothelialization, turbulent flow prevention, low profile constructs, enhanced flexibility, disease regression, restored functionality of the biological duct and natural growth of the biological duct or a combination thereof.

In some embodiments, diameter enlargement will promote circumferential alignment of the fibers. This will enhance the load bearing capacity of the stent and benefit native-like tissue formation. Cells can align along the fibers of the construct and produce tissue component such as collagen in the same direction, resembling the native configuration.

In some embodiments rearrangement of the fibrous network could lead to fiber stretch. Hereby the fibers can be elongated without resulting in a brittle behavior that causes failure of the construct upon expansion. Fiber stretch could benefit the local mechanical fiber properties on a molecular level by aligning the polymer chains, which might result in a stiffening effect of the fiber.

Method of Making

Figure 3A:
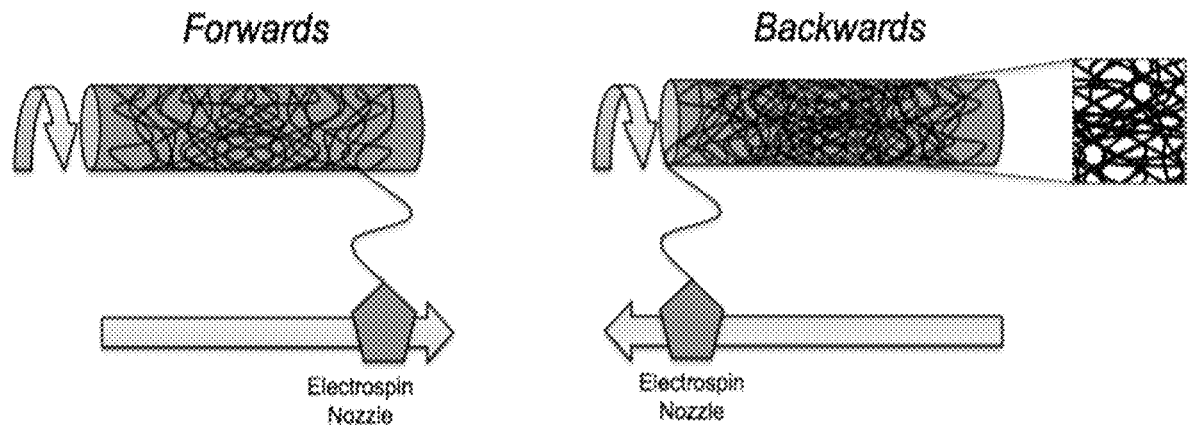
FIGS. 3A-B show according to an exemplary embodiment of the invention an example how constructs can be created using electrospinning, and how random (FIG. 3A) and controlled (FIG. 3B) fiber orientations could be obtained.

In an exemplary embodiment, fibrous tubular conduits could be produced by using electrospinning technology. A biodegradable polymer can be dissolved in a solvent to obtain a polymer solution. This solution could contain either a single polymer or multiple polymers into a blend. The polymer solution is guided towards the nozzle of the electrospinning equipment. A rotating mandrel is positioned in front of the nozzle at a set distance. A voltage difference is applied over the nozzle and the mandrel, by which a taylor cone is formed in front of the nozzle. From this taylor cone, a continuous polymer jet is ejected towards the mandrel. Since the mandrel is rotating, the polymer fiber is wrapped around the target. By moving the nozzle back and forward over the length of the target, the length of the electrospun scaffold can be defined (FIG. 3A).

Figure 3B:
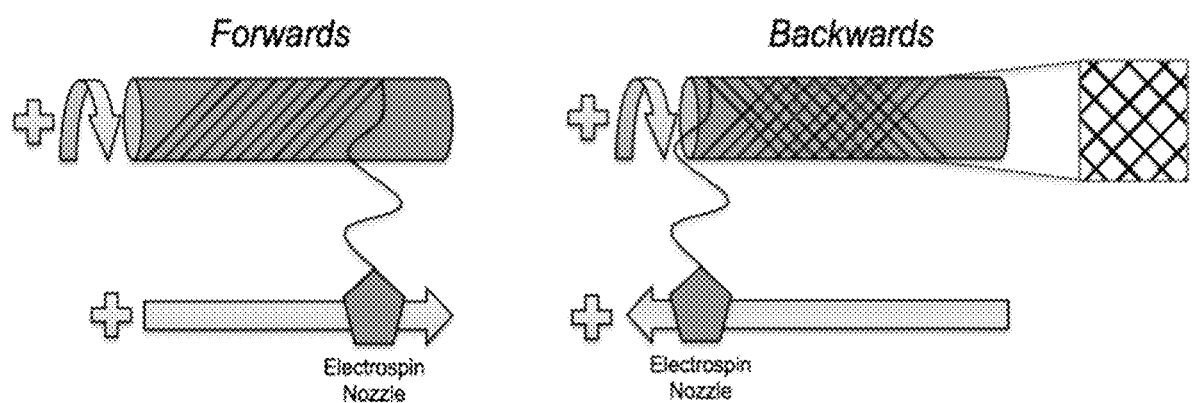

To control the orientation of the fibers on the target, from a random towards an aligned configuration, electrospinning settings can be adjusted. There are multiple possible parameter combinations to reach this state. One example is to increase the rotation speed of the mandrel, by which fibers will be more circumferentially aligned on the target (FIG. 3B). To control the angle of the fibers relative to the symmetry axes of the target, the travel speed of the nozzle can be adjusted while spinning aligned fibers. By defining the rotational speed of the mandrel, the appropriate travel speed of the nozzle can be calculated, to reach a controlled fiber angle. The travel speed, both in forward and backward direction, can be set separately in order to create one or multiple main fiber angles. When preferred, multiple nozzles can spin on the same target under different conditions to simultaneously use multiple polymer materials. Also both random and aligned fibers could be spun simultaneously onto one target by changing individual conditions from multiple nozzles. By setting the spinning time, the wall thickness of the scaffold can be controlled. Electrospinning settings, the composition of the solvent as well as the concentration of the polymer solution can be adjusted to control fiber diameter and pore size.

Other production methods to produce similar fibrous constructs could be, emulsion electrospinning, coaxial electrospinning, melt electrospinning, electrostatic drawing, braiding, weaving, knitting, additive manufacturing, 3D printing, bioprinting, electro spraying, polymer jetting, injection molding, casting or any other fiber production method or a combination thereof.

After manufacturing, the fibrous network might require an annealing step. Annealing is a heat treatment that can alter the physical and or chemical properties of a material. In some cases the fibrous network will be heated above the Tg. The annealing temperature will be maintained for a defined period of time followed by a cooling phase. Annealing can be performed in several steps, each step can have various repetitions and durations between cycles and between repetitions.

The optimum material to manufacture the construct depends on the biological duct where it will be inserted and the nature of the disease to be treated. Biocompatible materials can include:

bioresorbable polymers (such as poly lactic acid (PLA), including poly(L-lactide), poly(D-lactide), poly(D,L-lactide), as well as polyglycolid acid (PGA), polycaprolactone, polydioxanone, poly(trimethylene carbonate), poly(4-hydroxybutyrate), poly(ester amides) (PEA), polyurethanes, poly(trimethylene carbonate), poly(ethylene glycol), poly(vinyl alcohol), polyvinylpyrrolidone, and copolymers thereof), non bioresorbable materials (such as polypropylene, polyethylene, polyethylene terephthalate, polytetrafluoroethylene, polyaryletherketone, nylon, fluorinated ethylene propylene, polybutester, and silicone, or copolymers thereof), biological components (such as hyaluronan, collagen, gelatin, chitosan, alginate, aloe/pectin, cellulose or other biological materials originating from tissues from either autologous, allergenic or xenogenic origin), or a combination thereof.

The polymers can be of the D-isoform, the L-isoform, or a mixture of both. Multiple polymers and copolymers can be mixed and blended into different ratios. The polymer fibers can be crosslinked. Some embodiments may include supramolecular chemistry including supramolecular polymers, linking mechanisms or moieties. Some embodiments may comprise shape-memory polymers.

In some embodiments multiple fibrous layers with different densities can be combined. Cell infiltration, and hence tissue formation, can be prevented or enabled by adjusting the porosity of a fibrous layer. Adjusting fiber spacing and/or fiber diameter and layer thickness can alter the conditions for cell infiltration. In this way cell infiltration and migration can be controlled with dense structured layers, which face either the outer and/or luminal side of the construct.

Impermeable layers can be added based on either densely packed fibers, porous structures with high surface tension or non-porous networks, to prevent fluid leakage; for purposes where for instance lesions or ducts need to be closed.

In some embodiments, speed of bioresorption can be tuned by acting on the molecular weight of the polymer, combining polymers with different intrinsic bioresorption speed and/or modifying the porosity of the fibrous network, the fiber diameter and/or the number of layers of stacked fibers.

Method of Testing/Evaluating

To evaluate the fiber distribution and orientation of the fibers from the fibrous network, microscopic images can be obtained for instance by using scanning electron microscopy. After obtaining the macroscopic picture, image analyses software can be used to calculate the obtained fiber distribution and orientation. One example of a free image analysis software is Fiji (ImageJ). By using the directionality plugin, the fiber orientation and distribution is calculated by either using Fourier components or by calculating a local gradient orientation to analyze the image. The software will fit a mathematical distribution to the data, which in the standard configuration is a Gaussian distribution. In this way, both fiber dispersion ($\sigma$) as well as the main fiber angle ($\alpha$) can be obtained, where the fiber angle is the center, and the dispersion the standard deviation of the Gaussian fit.

To enable minimally-invasive implantation and anchoring of the construct, the diameter needs to be enlarged once it is positioned at the desired location inside the biological duct. Diameter enlargement of the construct is facilitated by making use of fiber reorganization of the fibrous network from which the construct is composed of To discriminate between the initial and expanded states, we define state 1 as being the construct after production, and state 2 as being the same construct after diameter enlargement. The construct can act as a stent when reaching state 2. In order to enable diameter enlargement, fiber reorganization between state 1 and state 2 has to be induced. The fibrous network of the construct in state 1 could have a random fiber organization (Scenario A) or a controlled fiber organization (Scenario B), or a combination there of.

Scenario A: Random Fiber Orientation

Figure 5A:
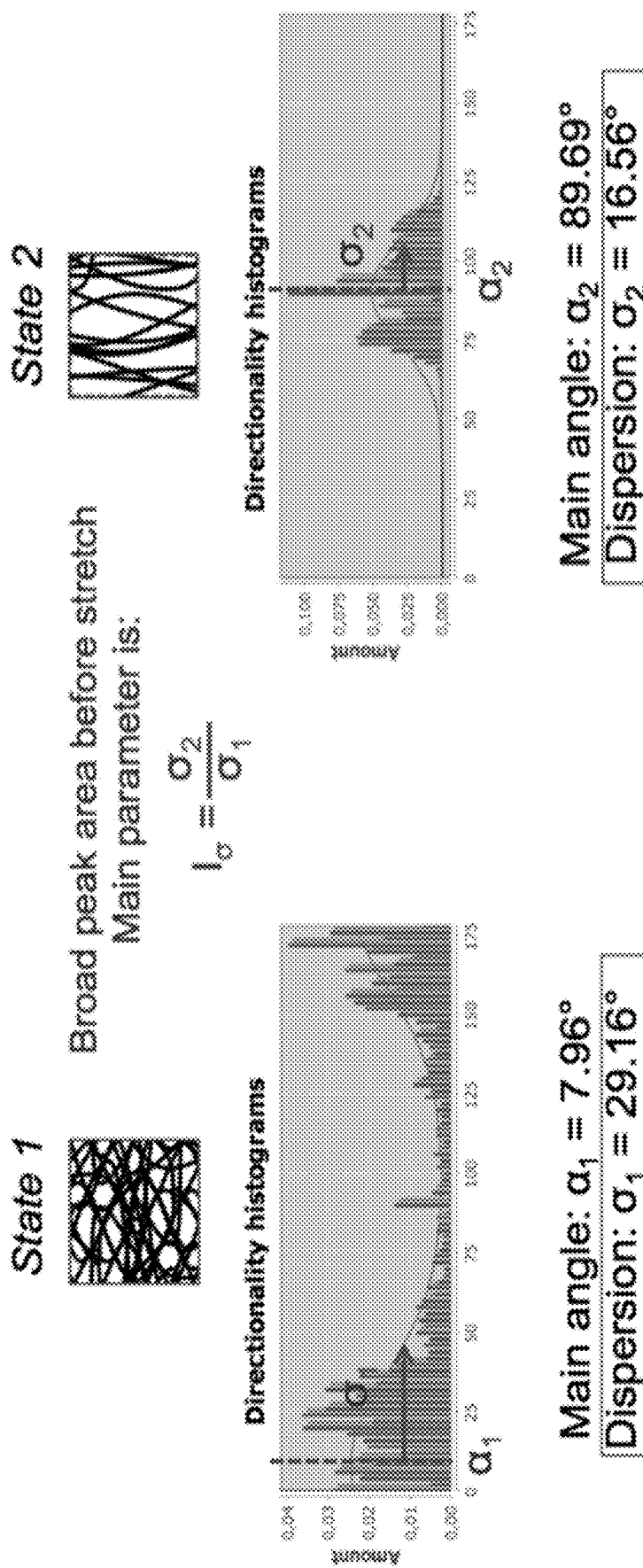

State 1: is defined as a scaffold having fibers randomly oriented (FIG. 4A). The directionality histogram describes a broad peak area with several maximums of high intensity defining a rather flat Gaussian fitting curve (FIG. 5A). This is captured by a relatively high value of fiber dispersion 6. In this case, the fiber angle $\alpha$ merely describes the center of the Gaussian curve with no real physical relevance.

Figure 2:
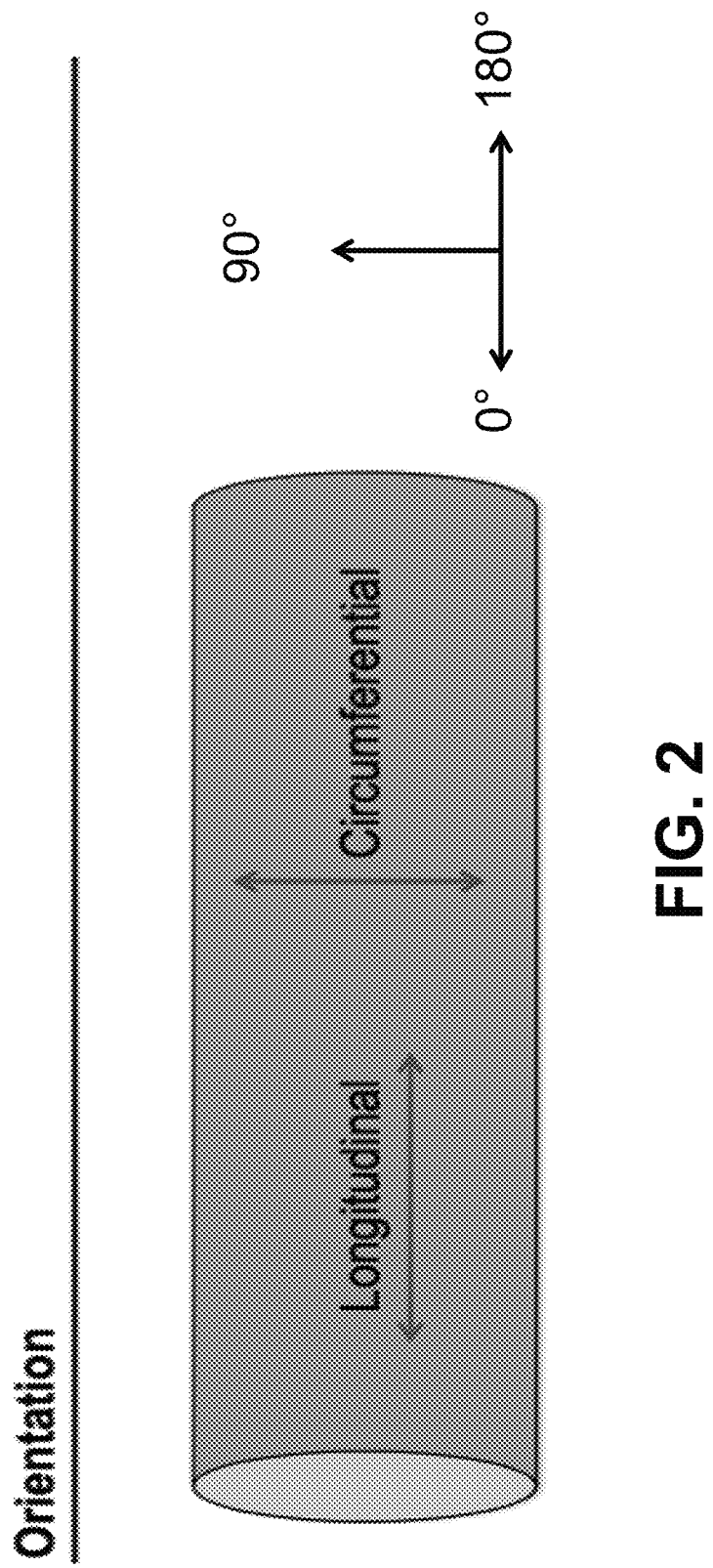
FIG. 2 shows according to an exemplary embodiment of the invention defining the orientation of the construct respectively to the fibers (FIG. 2).

State 2: the diameter of the scaffold from state 1 has been enlarged resulting in state 2, which causes realignment of the fibers (FIG. 4A). The directionality histogram describes a narrowed peak area surrounding one preferred orientation (FIG. 5A). This is captured by a lowered value of $\sigma$ and a value of $\alpha$, which approaches 90 degrees, here defined as the circumferential direction (FIG. 2).

The relevant parameter here is $\sigma$. To prove fiber alignment, the degree of fiber dispersion is quantified by comparing $\sigma$ from state 1 ($\sigma_1$) with $\sigma$ from state 2 ($\sigma_2$), resulting in a realignment index, which is defined as $I_\sigma = \sigma_2$ divided by $\sigma_1$, and can describe any range between no alignment ($I_\sigma = 1$) or complete alignment ($I_\sigma = 0$). Any $I_\sigma < 1$ confirms that fiber reorganization is induced to enable the transition from state 1 to state 2 (FIG. 6).

For the sake of clarity, even a small degree of realignment is crucial because it enables diameter expansion without the need of a strut pattern, unlike conventional stents that usually relay on macroscopic voids to enable expansion. Here, lower values of the realignment index are expected to have favored mechanical properties.

Scenario B: Controlled Fiber Orientation

State 1: is defined as a scaffold having fibers distributed in one or more main orientations. The directionality histogram in this example describes two main orientations by two narrow peaks defining the main angles $\alpha_1$ and $\alpha_2$. The fiber dispersions $\sigma_1$ and $\sigma_2$ are low (in agreement with the high degree of fiber alignment in both directions).

State 2: the diameter of the scaffold from state 1 has been enlarged to result in state 2, which causes reorientation of the fibers. The directionality histogram describes two narrow peaks, which have become closer to 90 degrees describing circumferential alignment. Clearly the relevant parameter here is $\alpha$. However the main angle difference ($\Delta\alpha$) describes the existence of two families of fibers and the reduction of $\Delta\alpha$ between states describes the alignment. The reorientation index is defined as $I_{\Delta\alpha} = \Delta\alpha_2$ divided by $\Delta\alpha_1$, and can describe any range between no reorientation ($I_{\Delta\alpha} = 1$) or complete reorientation ($I_{\Delta\alpha} = 0$). Any $I_{\Delta\alpha} < 1$ confirms that fiber reorientation is induced to enable the transition from state 1 to state 2 (FIG. 6).

The construct can be balloon expandable. Here a tubular construct can be produced to meet state 1. The construct is mounted over the balloon of a balloon catheter. The construct might be annealed over the balloon to facilitate proper fixation of the construct. Upon implantation, the balloon will be inflated and the construct will be deployed into the biological duct. Upon deflation of the balloon, the construct will reach state 2.

The construct can be self-expandable. Here a construct can be produced in a larger diameter and be crimped to reached state 1. The stent is loaded into a shielded catheter device. Upon implantation the shield will be removed and the stent will be deployed into the biological duct to reach state 2.

In one of the embodiments of the invention, the fibers will be exposed to a circumferential stress upon expansion. Fibers will be stretched circumferentially and interconnections will be overcome resulting in diameter enlargement of the structure without exhibiting a brittle behavior. In this way, the fibrous network has rearranged to enable diameter enlargement. In state 2, the enlarged construct will support the load of the biological duct where it has been implanted to act as a stent, which will be enabled by a suitable selection of the material and the mechanical properties that prevent collapse of the structure.

Comparison

Fibers in current stents in the art, are not or will not be reoriented and/or realigned, stretched and/or straightened upon enlargement of stent diameter. Those fibers could possibly change orientation due to rotation by opening of the strut pattern. However, in case those fibers were randomly oriented in state 1, they would remain random in state 2. This makes $I_\sigma = 1$. Furthermore, in case those fibers were controlled oriented (aligned in circumferential direction) in state 1, they would become less circumferentially aligned in state 2. In that case $I_{A\alpha}>1$.

Overcoming the Interconnections

As described supra, fibrous tubular conduits can be implanted minimally-invasively to support biological ducts. Upon expansion, fiber reorganization is essential to achieve diameter enlargement without compromising the integrity of the construct, where after the reoriented fibers need to guarantee proper anchoring of the construct and patency of the biological duct. For this purpose, not only the mechanical behavior of the single fiber needs to be considered, but also the interaction between fibers.

Fibers, held together by fiber interconnections, can form a tubular construct. Fibers can lie adjacent or on top of each other, which is defined as non-bonded interconnected fibers. Fibers can be merged while lying adjacent or on top of each other, which is defined as physically-bonded interconnected fibers. To ease fiber rearrangement upon diameter enlargement, fiber interconnections can be overcome. Overcoming fiber interconnections during diameter enlargement could enhance fiber mobility allowing them to straighten, reorient, elongate and/or slide; improving the stretchability of the tubular construct.

Figure 16:
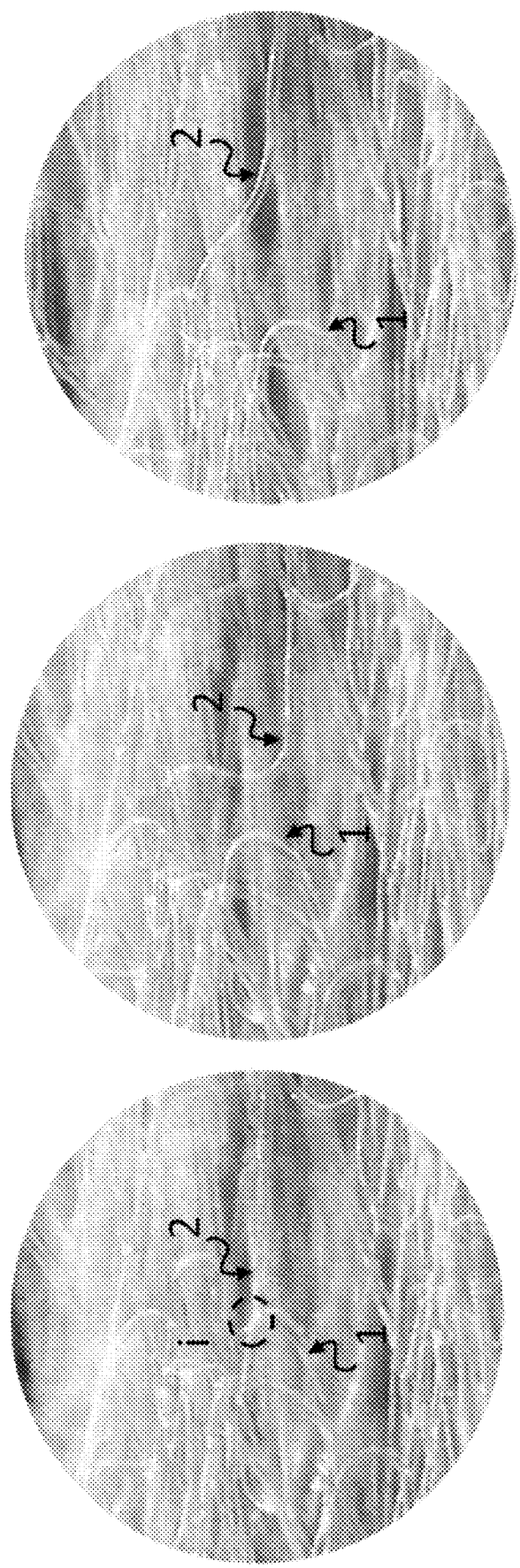
FIG. 16 shows according to an exemplary embodiment of the invention complete break of interconnection i of physically-bonded fibers, leaving individual fibers 1 and 2 intact.

The term "overcoming the interconnections" in this application means:
a) Sliding of non-bonded fibers, where the interconnection will be relocated. As shown in FIG. 15, two fibers are initially interconnected at point (1) where the interconnection is indicated by a circle (i). Initially (1) and (i) are coincident. As stretch is applied to the fibrous network, the interconnection (i) slides to a different location, differing in position with respect to point (1).
b) Breaking of the interconnection of bonded fibers, where the bonded interconnection can be seen as predefined breaking point. In this case stress will be accumulated at the interconnection which will eventually break:
b1) completely: leaving both fibers intact. As shown in FIG. 16, two fibers (1) and (2) are bonded at the interconnection (i). As stretch is applied to the fibrous network, the interconnection disappears and the fibers become independent;
b2) partially: segmenting one of the fibers. As shown in FIG. 17 two fibers (1) and (2) are bonded at the interconnection (i). As stretch is applied to the fibrous network, the interconnection is disrupted and fiber (1) has been separated in two fragments.

Relocating the interconnections could be essential to secure mechanical integrity of the expanded fibrous graft.

Wettability

Wettability is an important factor that can affect the rearrangement capacity of the fibrous network in an aqueous environment. Tuning the wettability of the fibrous network can affect the mechanical properties and biological interactions, and the degradation speed of the fibers as well as the interconnections, by which rearrangement of the fibrous network can be eased. The wettability of the fibrous structure has to be tuned in such a way that it allows for rearrangement of the fibers residing in the fibrous network upon diameter enlargement, but in addition needs to allow the rearranged fibrous network to maintain the mechanical load applied by the biological duct.

On the level of the fibers, tuning the wettability could influence (but is not limited to);

the capacity of water to penetrate into the polymer and hence could influence:
the Tg and Tm of a (co)polymer by which the mechanical characteristics may be altered.
the degradation speed of the polymer caused by bulk hydrolysis
the capacity of biological substances (such as but not limited to cells, proteins and enzymes) to adhere to the fiber or limit/prevent adhesion to act as a non-fouling surface;
the degradation speed of the polymer caused by surface hydrolysis.

On the level of the fiber interconnections, tuning the wettability could influence (but is not limited to):
the sliding capacity of non-physically bonded fibers by which friction between the fibers will be altered to act as a lubricant and favors the mobility of individual fibers
the sliding capacity of non-physically bonded fibers caused by attractive forces between hydrophobic surfaces.
the capacity of water to infiltrate into the fiber interconnections, hence could act as a plasticizer/solvent by which the physically bonded fibers could be overcome.

Relocation of non-bonded interconnections or creation of new physically-bonded interconnections, either prior, upon or post implantation, could be beneficial to improve mechanical support and for shaping purposes to include for instance sinuses, convex/concave shapes, curvature and/or, shaping voids to enable access to side branches, etc. In addition, this would be an attractive method to pre-shape other types of fibrous structures such as heart valve geometries. Shaping might require additional constraints to induce the desired geometry and might require additional annealing steps. Relocation or creation of new interconnection can be achieved by several means but not limited to, thermal treatment, chemical treatment, photo- or ultrasound activation, etc., either in-vivo or ex-vivo.

This invention further describes methods to tune the wettability of the fibrous network and facilitate fiber rearrangement.

Methods to Facilitate Rearrangement of the Fibrous Network

Surface Treatment

The fibrous network can undergo a high-energy surface treatment such as plasma, ultra-violet or radiation to cause modifications on a chemical and physical level on the polymer surfaces. This increases surface wettability when exposed to an aqueous environment. This will ease rearrangement of the fibrous network.

Surface Coating

Besides surface treatment, coating the fibers with a hydrophilic material can also increase wettability when exposed to an aqueous environment. It should be taken into account that applying a coating could greatly affect the mechanical integrity of the fibrous conduit, where coatings could act as lubricants or gluing agents when being applied to fibrous graft applications.

Increasing Temperature

The temperature of the environment at which diameter enlargement of the fibrous conduit takes place also affects wettability of the aqueous solution on a polymer fiber surface, where higher temperatures will improve this effect. The aqueous solution could either be water or blood, mixed with or without an alcohol. The effect of temperature on the wettability has a higher influence on low alcohol concentrations and short chain alcohols, compared to high alcohol concentrations and long chain alcohols. Temporarily enhancing the temperature at the side of implantation could therefore ease rearrangement of the fibrous network.

Alcohol as an Additive to the Aqueous Solution

Alcohols are good additives to increase the wettability of hydrophobic polymer surfaces in an aqueous solution. Longer alcohol chains could progressively enhance this effect by either lowering the surface tension of the aqueous solution and/or binding of the alcohol molecules to the imperfections of the fibers. In other words, by adding alcohol to an aqueous solution, a solvent film will be formed over the surfaces of the fibers that will enhance the mobility of fibers, easing fiber rearrangement and facilitating diameter enlargement of the conduit. When the preferred diameter has been reached, the medium could be replaced or depleted from the alcohol to reverse this effect.

The use of alcohols such as ethanol could also have a swelling effect at the surface of several polymers; thereby breaking the junctions of bonded fibers, before or during strain application. This could improve fiber mobility and ease rearrangement of the fibrous network allowing them to slide over one another, and should be translated in a considerable increase in stretchability of the construct. After removal of alcohol from the aqueous solution, swelling will be reversed and could restore bonding of the fibers, caused by evaporation of the solvent and concomitant adhesion and interaction between the solvated polymer chains at the site of anchoring. In this way, the stretchability of the fibrous conduit could be temporarily increased during diameter enlargement and the structural support could be restored after removal of alcohol from the medium.

In addition, the use of alcohol could have a plasticizing effect on the material via influencing the glass transition temperature (Tg) and/or the melting temperature (Tm) and respective melting enthalpy ($\Delta Hm$). This could enhance the flexibility of the fibers and contribute to make the construct more stretchable.

Alcohol could be incorporated inside the fibrous tubular constructs by immersing the graft in an aqueous alcohol solution, or by incorporating an alcohol gel within the structure. Such a gel could be produced by spinning separate fibers from poly(ethylene glycol) (PEG) based polymers (which have the ability to form a hydrogel), in addition to the base material fibers (i.e PLA) and immersing the construct in an aqueous alcohol solution to form the gel prior to implantation. The benefit of the alcohol gel is that it will remain stable within the construct during implantation for a certain period of time, promoting stretchability of the structure to allow for diameter enlargement. At the final diameter and by dissolution of the gel, the structure will recover its load bearing function.

Adjusting the Polymer Composition

Rearrangement of the fibrous network can be eased by acting on the polymer composition. Including components with different mechanical properties (such as elongation at break or elastic modulus) can enhance the stretching behavior.

In addition, blending or mixing polymers or creating a copolymer with components of different hydrophobic or hydrophilic characteristics can be incorporated to modify the wettability of the fibers, easing fiber rearrangement without compromising the structural capabilities of the construct. This method is more consistent with an in-vivo scenario where the addition of alcohol upon expansion would be less preferred.

Other methods to ease the rearrangement of the fibrous network without affecting the wettability of the fibrous network is to lower the strain rate during diameter enlargement of the conduit during implantation. Lowering strain rates will ease the rearrangement of the fibrous network Methods of Testing/Evaluating The degree of wetting can be measured by analyzing the contact angle ($\Theta$) of a liquid droplet on a solid surface. A high contact angle means that the surface is hydrophobic. A low contact angle means that the surface is hydrophilic, indicating good wettability of the surface with respect to the liquid. By placing a liquid droplet on a solid surface, $\Theta$ can be visualized by microscopy and quantified by imaging. An improvement in stretchability can be assessed using mechanical analyses such as uniaxial tensile testing. Improved stretchability is expected to result in an enhanced elongation at break and a decrease in the force that is required to elongate the fibrous structures. In addition, a suitable performance and functionality of the construct can be evaluated by implantation in an animal model and subsequent follow-up, where the construct must prove to be competent as a stent that can be delivered minimally-invasively and as a scaffold that can induce tissue formation, hence as act a regenerative stent.

Example 1

Figure 8:
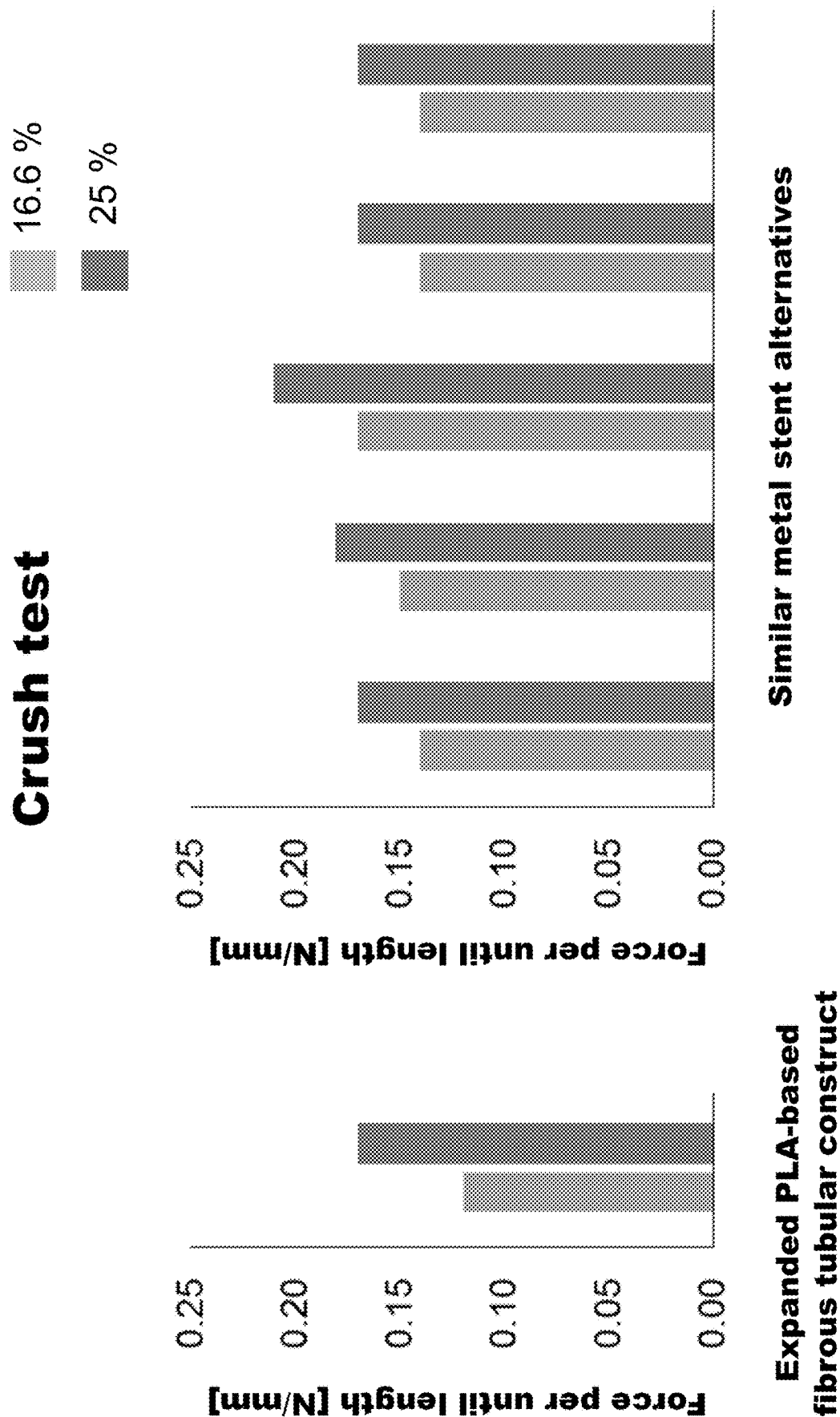
FIG. 8 shows according to an exemplary embodiment of the invention how simultaneous diameter enlargement and load bearing capacity can be simultaneously obtained after transition to state 2 for a PLA-based electrospun scaffold immersed in an ethanol solution to enhance stretchability and evaluation of the crush force after subsequent evaporation of the alcohol.

A 2 mm electrospun PLA-based tubular graft was immersed in an ethanol solution and subsequently expanded with a balloon, duplicating its diameter. The tube was dried evaporating the alcohol and the structure showed a load bearing capacity comparable to metal stent alternatives of similar dimensions reported in literature (FIG. 8)

Example 2

Figure 9A:
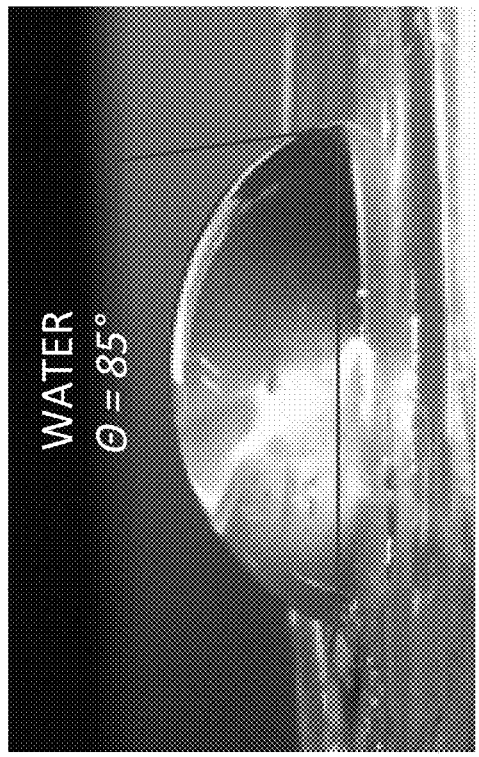
FIGS. 9A-D show according to an exemplary embodiment of the invention how different aqueous alcohol solutions (FIGS. 9A-D) in contact with the PLA based solid surface affects the wettability of the polymer surface. The contact angle of alcohol droplets on the PLA surface was calculated to determine the wettability. Pure water without alcohol had a contact angle of 85°, by mixing water with 25% methanol the contact angle dropped to 60°, with 25% ethanol to 45° and with 25% 1-propanol to 20°. Here, a method of using longer chain alcohols is used to increase the stretchability of PLA constructs in a laboratory setting.
Figure 9B:
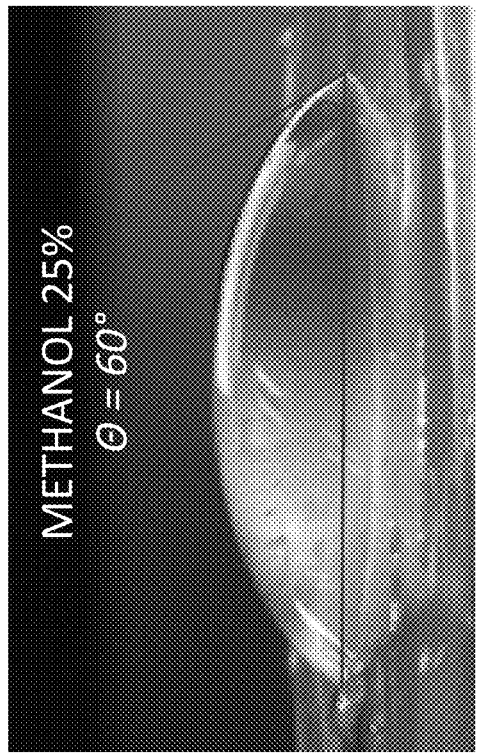
Figure 9C:
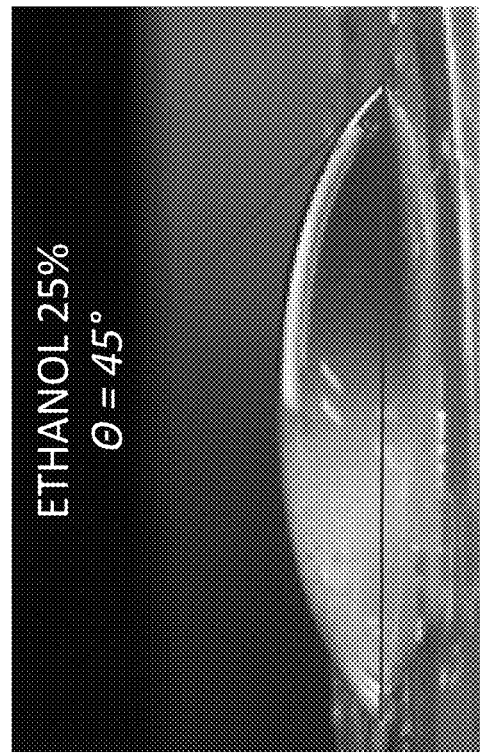
Figure 9D:

To assess the influence of alcohols on the wettability of PLA in aqueous environment, solutions including alcohols with increasing chain length where prepared and the resulting contact angles formed over a solid PLA surface were compared to pure water. The addition of pure water on the PLA substrate resulted in a contact angle of 85° (FIG. 9A) that lowers to 60° after including 25% of methanol (FIG. 9B), to 45° with 25% of ethanol (FIG. 9C) and to 20° with 25% of 1-propanol (FIG. 9D).

Example 3

Figure 10:
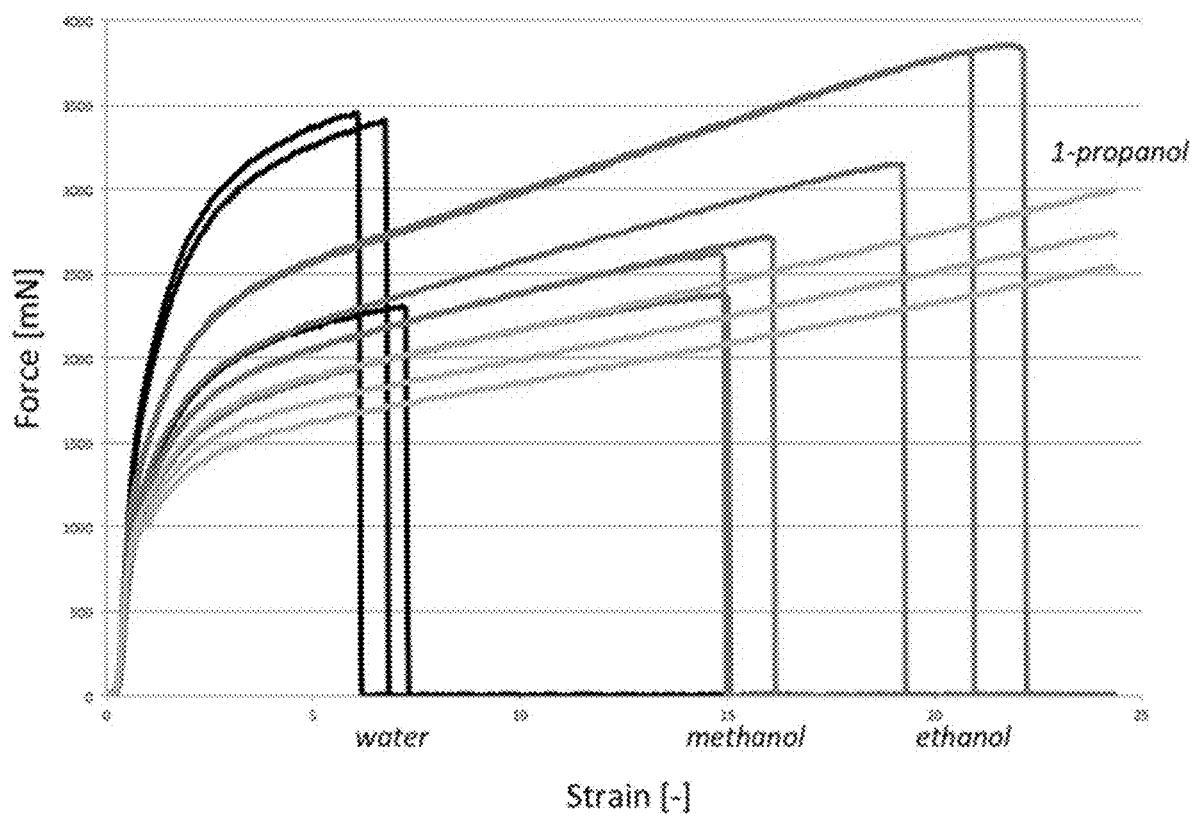
FIG. 10 shows according to an exemplary embodiment of the invention the effects of adjusted wettability properties of the polymer fiber surface on the mechanical properties of PLA based fibrous conduits, using different alcohols. Including methanol resulted in an increase of elongation at break 2.5 times compared to pure water whereas ethanol represented an increase of 3.67 times and 1-propanol even prevented ring rupture. This confirms that increasing the wettability of the polymer fiber surface comprising the fibrous network, is translated in an increase of the elongation at break.

The effect of alcohol on the stretchability of PLA based fibrous tubular conduits was evaluated by uniaxial tensile testing at room temperature. Rings of 0.5 mm width were obtained from 20 mm electrospun PLA tubes after 1 hour spinning. Samples were immersed in pure water and in 25% solutions of the alcohol of interest and tested at a strain rate of 2.33 mm/s. Adding methanol resulted in an increase of elongation at break 2.5 times compared to pure water whereas ethanol represented an increase of 3.67 times and 1-propanol even prevented ring rupture (FIG. 10).

Example 4

Figure 11:
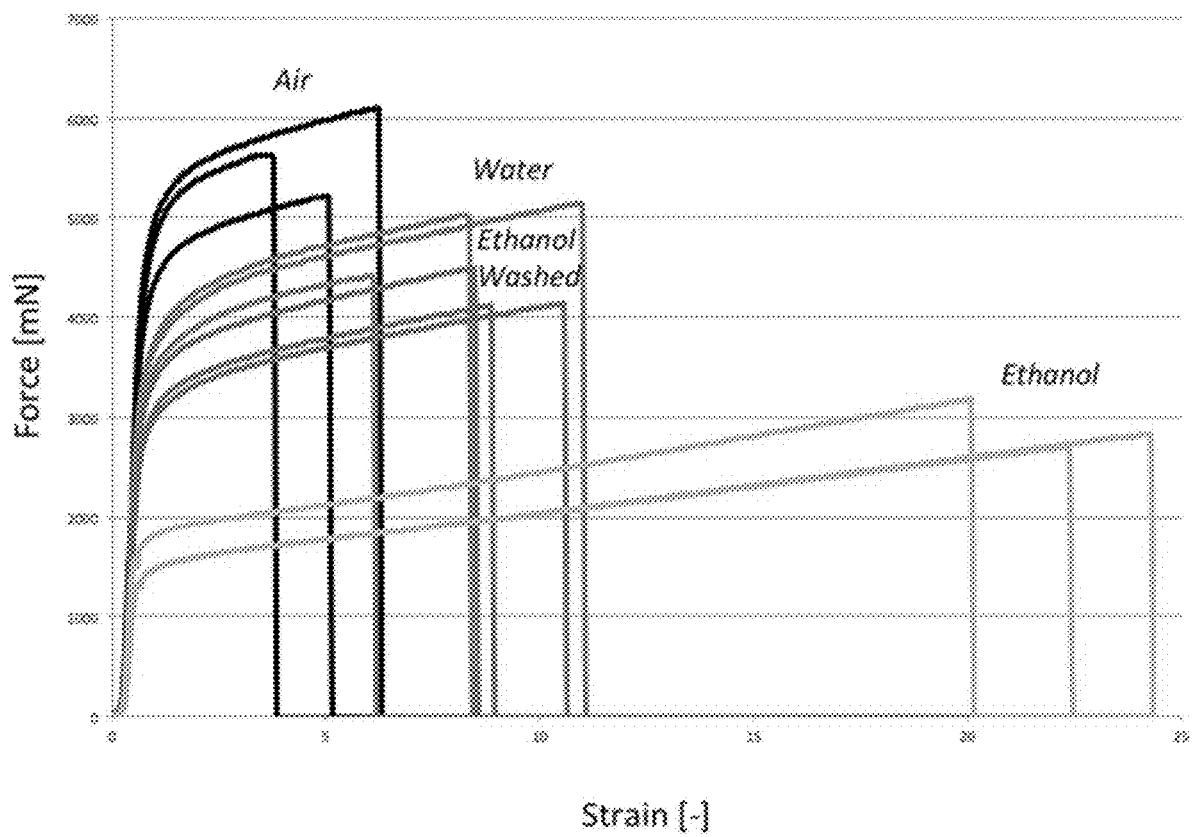
FIG. 11 shows according to an exemplary embodiment of the invention the effects of temporary adjusting the wettability of the fiber surface comprising the fibrous network using alcohol such as ethanol, on the mechanical properties of a PLA-based fibrous tubular conduits. Tests were performed on: i) dry electrospun rings, ii) rings immersed in pure water, iii) rings immersed in a 25% ethanol solution and iii) rings immersed in a 25% ethanol solution where after ethanol was depleted by multiple washing steps in water. This shows that ethanol has a temporary effect where after depletion, mechanical properties almost fully recovered.

The effect of alcohol on the mechanical properties of PLA-based fibrous tubular conduits after alcohol depletion was investigated using uniaxial tensile testing at room temperature. Tests were performed on: i) dry electrospun rings, ii) rings immersed in pure water, iii) rings immersed in a 25% ethanol solution and iii) rings immersed in a 25% ethanol solution where after ethanol was depleted by multiple washing steps in water. This example shows that ethanol has an effect on the mechanical properties of PLA-based fibrous tubular conduits, which is to a certain extent reversible (FIG. 11). Testing dry PLA-based rings puts in evidence the advantage of the electrospinning technique for the stretchability. Compared to the elongation at break of bulk PLA, electrospun PLA presents an increase of two orders of magnitude. Forces decreased when samples were immersed in water and even presented a more considerable decrease when immersed in an ethanol solution. After depletion of ethanol, forces are restored to values that are comparable to water immersion.

Example 5

Figure 12:
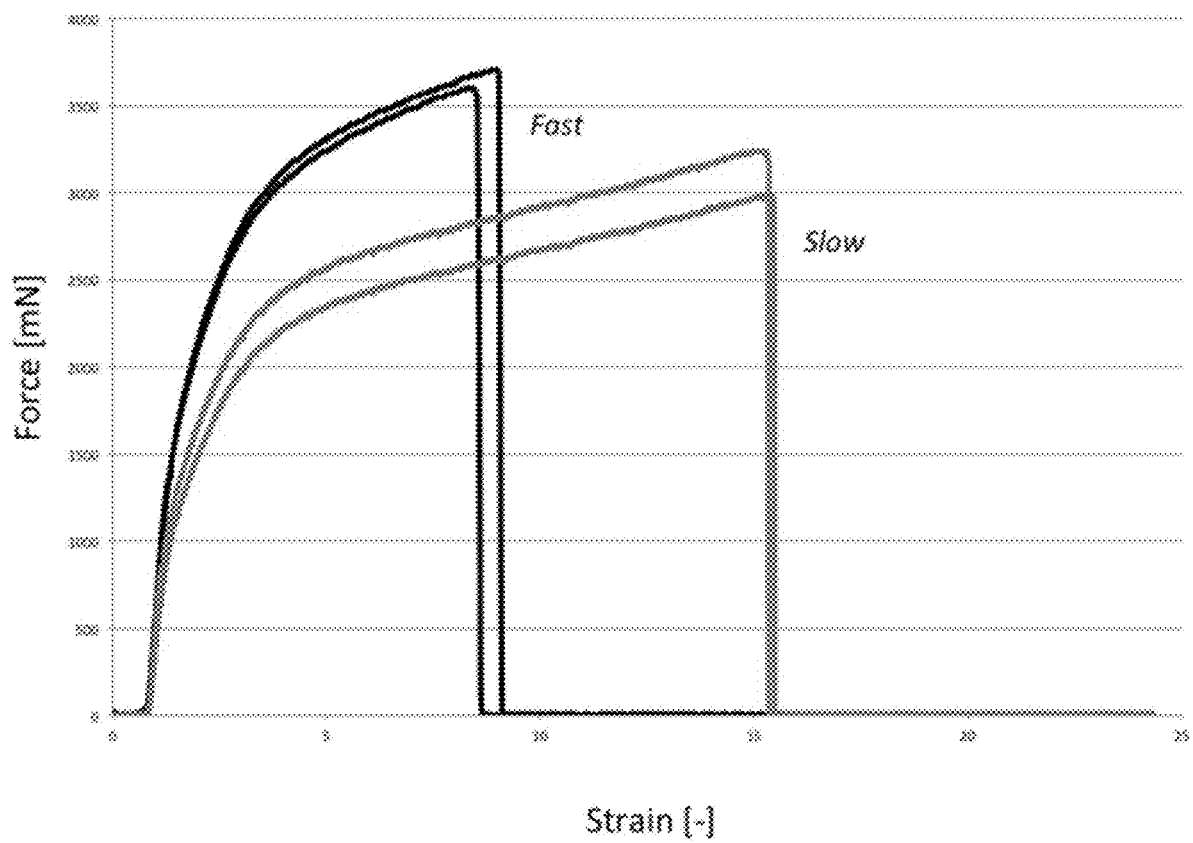
FIG. 12 shows according to an exemplary embodiment of the invention the effect of strain rate on the mechanical properties of PLA-based fibrous tubular conduits emerged in pure water. Lowering strain rates improves the fibers to reorganize enhancing the stretch capacity of the construct.
Figure 13:
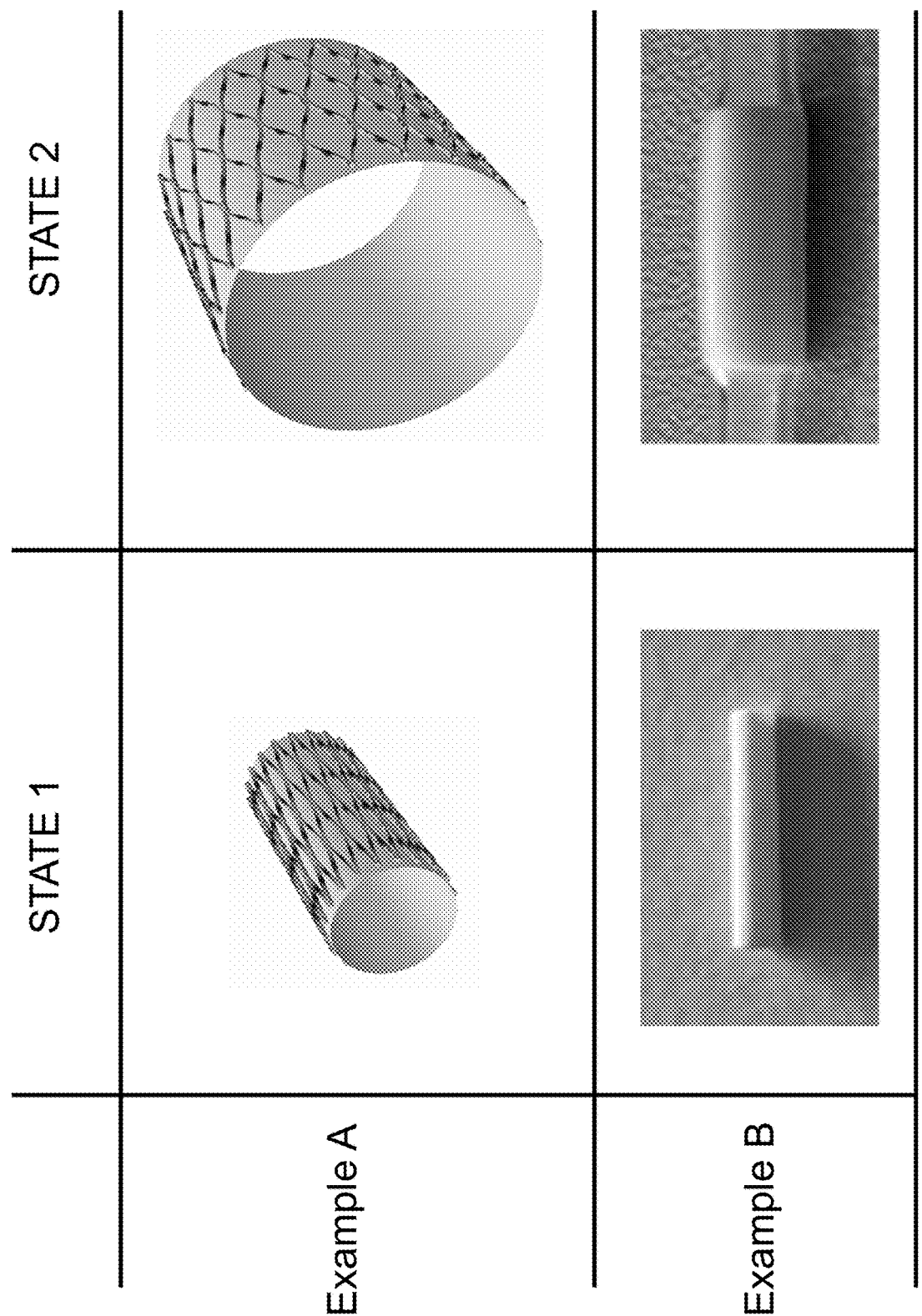
FIG. 13 shows in Example A a conventional concept of stent expansion based on a strut pattern. Out of a solid wall tube, a strut pattern is embedded to make the structure act as a stent. Expansion from state 1 to state 2 is enabled by the geometrical adjustment of the strut pattern, where the established open voids become larger. Example B, according to an exemplary embodiment of the invention, shows the concept of using fiber reorganization to allow for stent expansion. Expansion from state 1 to state 2 is solely enabled by reorganization of the fibers in the fibrous network, hence not relying on a strut pattern. Structural support in state 2 is shown by maintained diameter enlargement achieved in the silicon-mocking vessel.

Strain rate plays an important role in the mechanical behavior of PLA-based scaffolds. Uniaxial tensile tests of PLA-based rings were repeated decreasing the stretching speed to 0.023 mm/s (FIG. 12). Lowering strain rates may allow the fibers to reorganize and relax improving the stretch capacity of the construct.

Example 6

Figure 7:
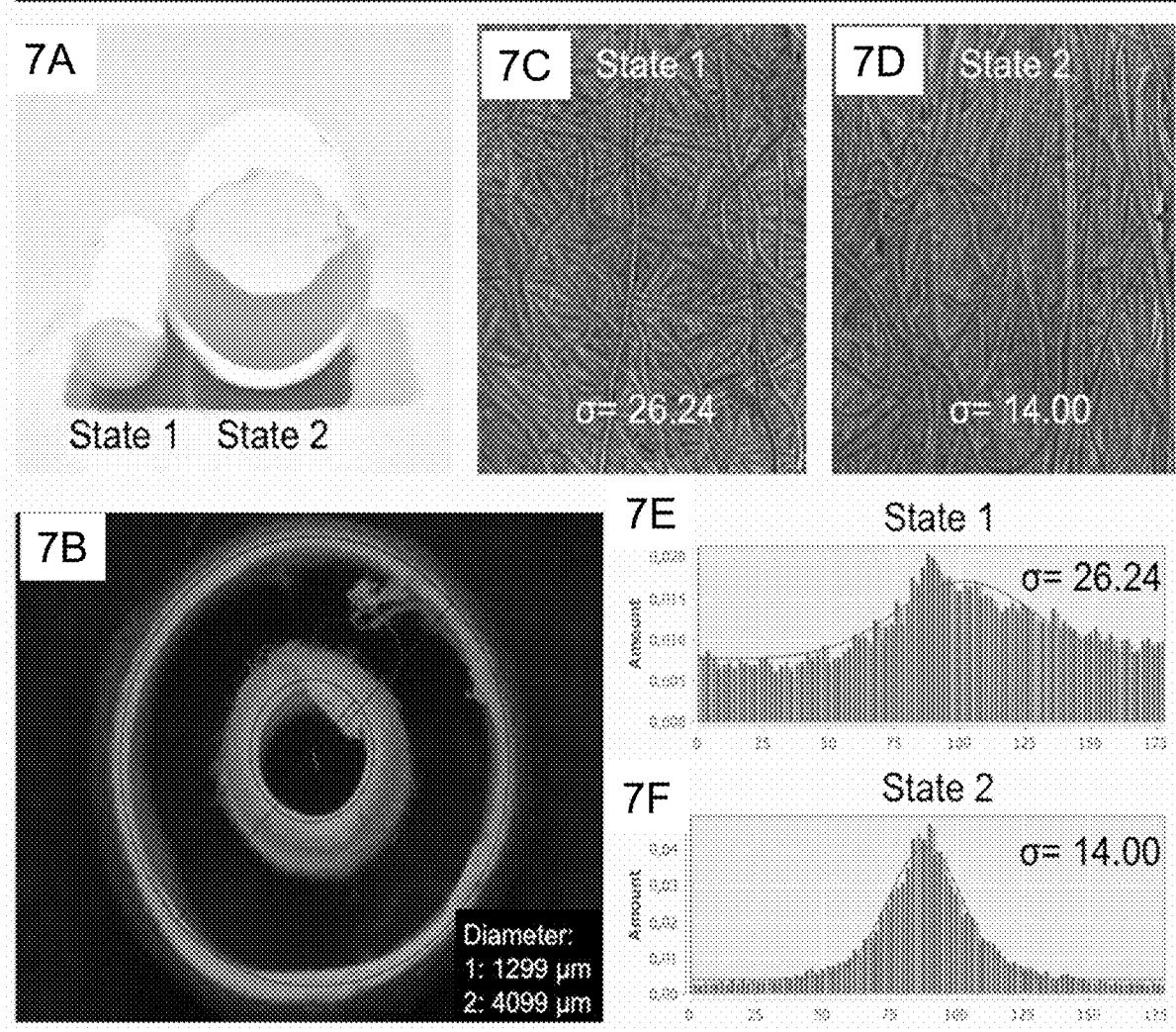
FIGS. 7A-F show according to an exemplary embodiment of the invention where a fibrous construct has been produced and expanded in diameter to transit from state 1 to state 2 (FIG. 7A). In this case the diameter has been enlarged to go from 1299 μm in state 1 to 4099 μm in state 2 (FIG. 7B). Microscopic pictures of the fibers were made by using scanning electron microscopy, when the construct being in state 1 and state 2 (FIG. 7C-D). The images were analyzed using image analyses software (Fiji, ImageJ), which determined a value for $\sigma_1=26.24°$ and value for $\sigma_2=14.00°$ (FIG. 7E-F). This results in a realignment index of $I_\sigma=0.53$, confirming the fiber reorganization.

A regenerative stent, were the stretchability of the construct has been enhanced by addition of alcohol to the aqueous solution where the construct was expanded (FIG. 7A). The construct can transition from state 1 to state 2 without compromising its integrity upon expansion (FIG. 7A). The diameter enlargement achieved upon balloon inflation is depicted in FIG. 7B. The fiber dispersion and histograms corresponding to both states are depicted in FIGS. 7 C, D, E & F.

Example 7

Figures 18A, 18B, 18C:
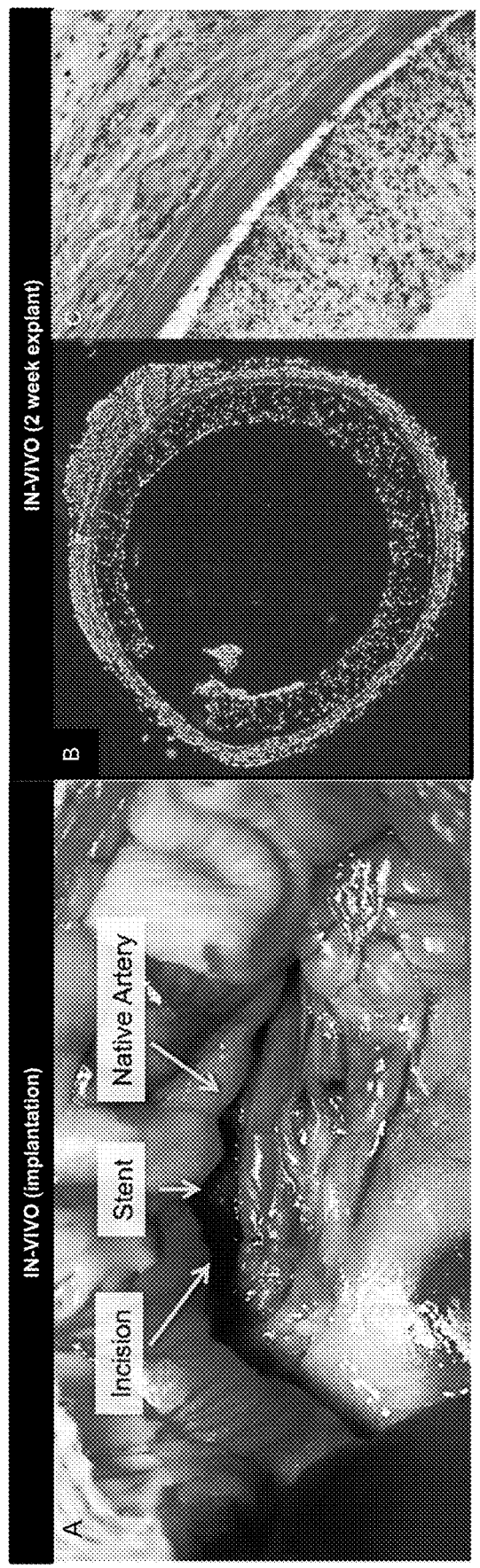
FIGS. 18A-C show according to an exemplary embodiment of the invention a regenerative stent implanted inside the abdominal aorta of a rat FIG. 18A, providing in-vivo evidence of minimally-invasive implantation of regenerative stents in an animal model.

A regenerative stent, were the stretchability of the construct has been enhanced by acting on the polymer composition has been minimally-invasively delivered in the abdominal aorta of a rat by balloon expansion (FIGS. 18A-C). This example illustrates a method to treat vascular diseases with one embodiment of our invention. The stent has been successfully deployed in the native artery by minimally-invasive methods (FIG. 18A). Furthermore, cells are able to infiltrate the construct and start producing tissue already two weeks after implantation (FIGS. 18 B-C). The regenerative stent has been expanded without relying on a strut pattern and has maintained its supportive capacity without compromising its integrity after implantation.

Methods of Using

Figure 19:
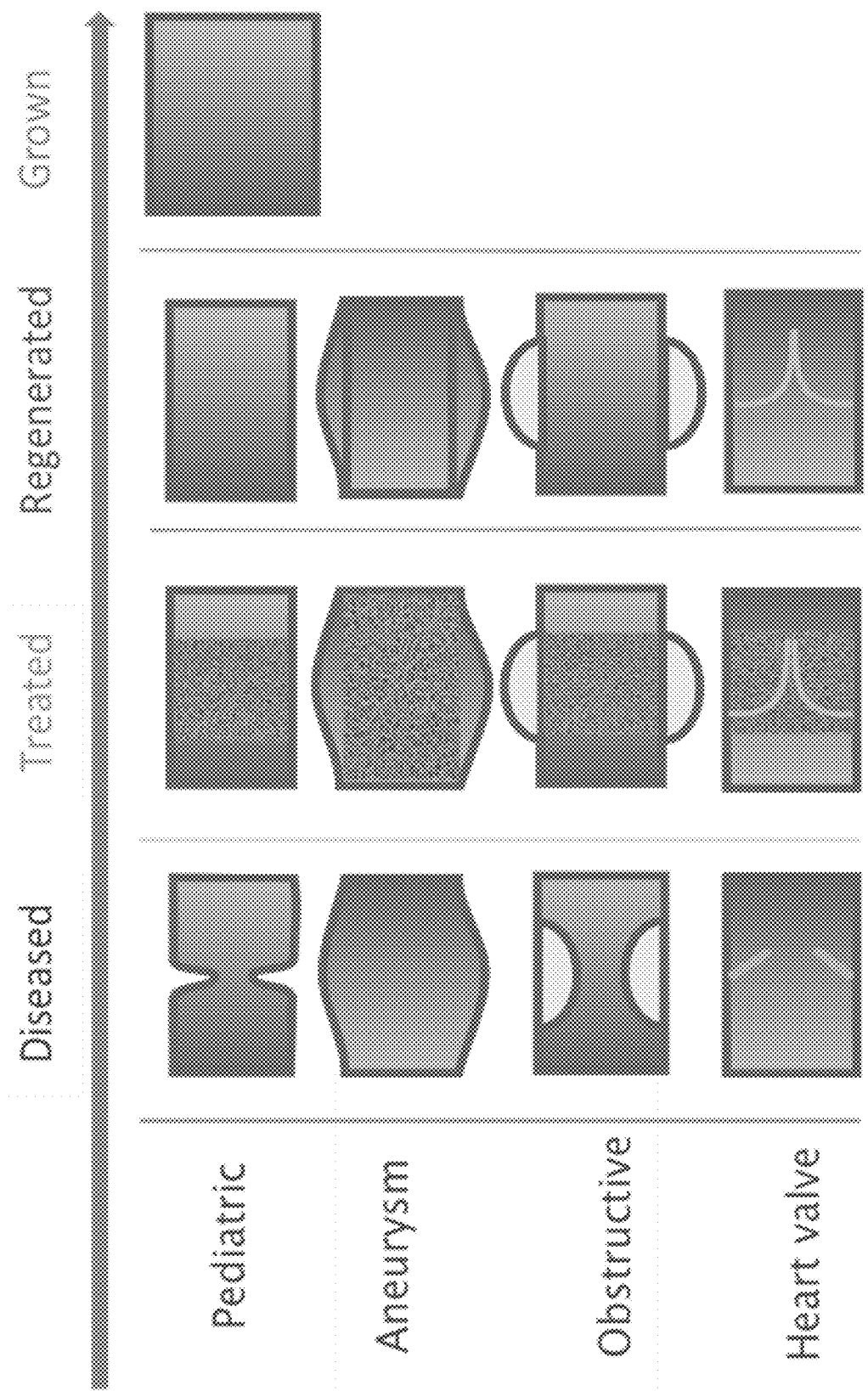
FIG. 19 shows according to an exemplary embodiment of the invention different types of clinically relevant vascular applications where regenerative stents can be used.

Various clinical indications could highly benefit from regenerative stents and bioabsorbable stents that do not present a strut pattern (FIG. 19). Each particular indication has distinctive features and requirements to be taken into account which, for the sake of clarity, should be evaluated case by case, further elucidate in some examples.

Example 1

Atherosclerosis is a disease that develops due to a deposit of fatty materials such as cholesterol in the arteries causing hardening of the vascular wall and narrowing of the artery. It is believed that the trigger and progression of atherosclerosis is related to inflammatory processes in the endothelial cells and/or smooth muscle cells of the vessel wall associated with retained low density lipid (LDL) particles. Current hypothesis suggest that a covering thin-cap fibroatheroma will induce plaque regression and formation of a thick shield of covering tissue. As regenerative stents will initiate the formation of a tissue layer on top of the fibrous cap, it could facilitate plaque regression.

Example 2

Aneurysms are locally weakened areas in a blood vessel that bulge outwards. As they fill with blood and are subjected to continuous cyclic pressure, aneurysms grow and become weaker over time where they could eventually rupture and lead to internal bleedings. Regenerative stents can fully shield the aneurysm and take over the load of the artery. As the blood flow inside the aneurysm is obstructed, a thrombus can be formed to fill the cavity. Over time a new artery will be created while the aneurysm will safely regress as the thrombus is being resorbed. Some embodiments can contain a fibrous network capable to act as a flow-diverting device.

Variations

In some embodiments, markers might be incorporated to enhance traceability through imaging of the device prior, during or after implantation. In some embodiments, contrast agents can be included. In some embodiments, the device can be further functionalized by including cell-capturing moieties either on the luminal side, inside the fibrous mesh or on the outside.

In some embodiments, agents like drugs or therapeutics can be incorporated, which can be immune modulative anti-inflammatory (such as steroids), anti-proliferative (such as everolimus), or be agents, which are therapeutic, prophylactic, or diagnostic. Agents can be antineoplastic, antiplatelet, anti-coagulant, anti-fibrin, antithrombotic, antimitotic, antibiotic, antiallergic, antioxidant, antiinfective, and cystostatic agents.

In some embodiments agents can affect biological processes, comprising but not limited to, bioactive agents from entire biological compounds such as cytokines, chemokines or other enzymes or peptides thereof from either biological or synthetic origin.

In some embodiments, the construct can be used as an agent vehicle. Agents can be incorporated into the fibers by mixing it into the polymer solution prior to conduct production. Agents can be coated on the fibrous surface after conduct production. Agents can be chemically linked to the fibrous network. Agents can be chemically linked by making use of supramolecular chemistry.

In some embodiments, agents will be released upon implantation. Agents can be released as the fibers are being absorbed and/or as the coating on the fibers will absorb over time. Secretion speed of the drugs can be controlled by tuning the degradation speed of the polymer/coating. Also changing the concentration of the included agent will influence the release profile. When agents are chemically linked, agent can be released as the chemical linker is being broken. Breaking the chemical link can be broken by temperature, pH, ultrasound, additive, or cytokines released by cells. Breaking the chemical links can happen without further interference, or can be controlled by specifically inducing the trigger that initiates chemical link breaking.

In some embodiments, agents can be incorporated into the embodiment to act on: cell infiltration, cell adhesion, tissue formation, tissue composition, selective cell recruitment, neointima tissue formation, endothelial cell adhesion, macrophage polarization, cell activation, induce angiogenesis, induce plaque regression in atherosclerotic regions, activate cell contractility, and/or induce tissue degradation.

Fibrous conduits can be positioned in front of a bifurcation or other opening after implantation, which can hamper passage of biological components. To facilitate patency to the obstructed area, the wall of the fibrous construct could be adjusted. In some embodiment, a medical device is able to penetrate the wall from the inside to the outside to reach the bifurcation (FIG. 21A). The medical device can be a balloon catheter that is able to inflate and induce local rearrangement of the fibrous network at the location of the bifurcation (FIG. 21B). After removal of the medical device, the bifurcation remains patent. In another embodiment a small hole is created inside the wall of the fibrous network either prior or after implantation. The hole is positioned in front of the bifurcation and provides patency. This hole can be reshaped by means of similar medical devices such as a balloon catheter when preferred.

Figure 21D:
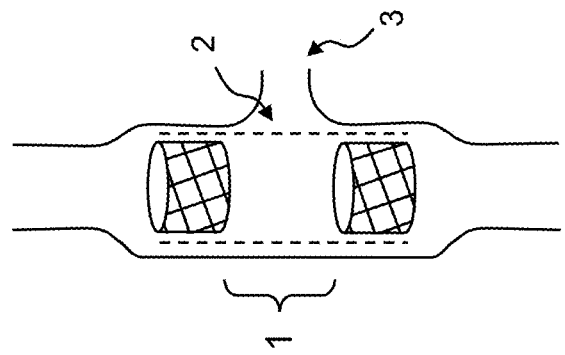
FIGS. 21A-D show according to an exemplary embodiment of the invention fibrous conduits can be positioned in front of a bifurcation or other opening after implantation.
Figure 21C:
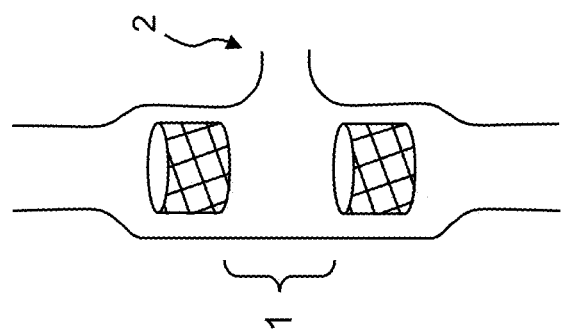
Figure 21B:
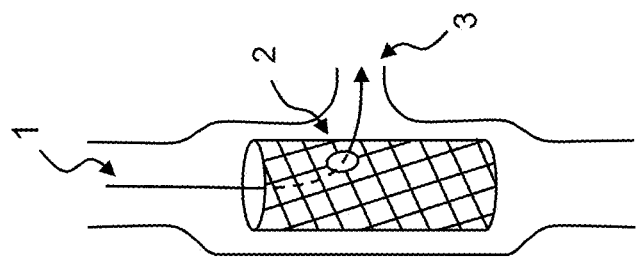
Figure 21A:
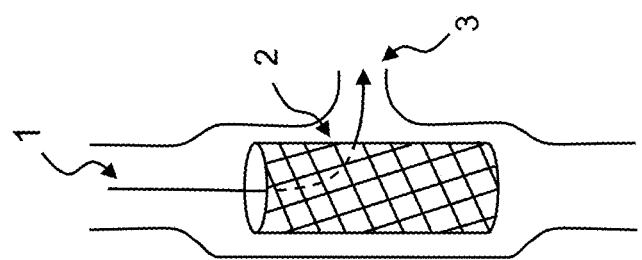

In an exemplarily embodiment, two constructs can be mounted onto a balloon catheter where there is a separation between another (FIG. 21C). After implantation of the stent this separation section can be positioned in front of the bifurcation to remain patency (FIG. 21A). In yet another embodiment two constructs can be mounted onto a balloon catheter where there is a separation between another, and a layer of fast absorbable materials can be included to cover the separation. After implantation of the stent the section with the separation covered by a fast absorbable material can be positioned in front of the bifurcation, where the fast absorbable layer can remain patency to the bifurcation after absorption.

The stent can contain additional embodiments.

Additional Embodiment 1

The stent can comprise a valve construct. The valve can contain one, two, three or multiple leaflets. The valve can be a mechanical, biological, or synthetic. A synthetic valve can comprise a fibrous network. Biological heart valves can be allografts, autografts or xenografts. The combined stent plus valve embodiment can be used to minimally-invasively replace valve structures such as the heart or in the veins. The components of an exemplary valved-stent are shown in FIGS. 20A-E. A valved stent can be composed of one or more layers and might require the use of special mandrels and molds to shape the leaflets, as well as surface treatments and annealing steps.

Addition Embodiment 2

The stent can comprise a cross-sectional membrane. The membrane can be biological, metallic or synthetic. The membrane can be permeable or impermeable. The membrane can facilitate or prevent fluid exchange. The membrane can facilitate or prevent passage of cells or selectively filter them. Filtering can be enabled by tuning the pore size of the membrane. Moieties can be included in the membrane to selectively adher to cells, enzymes or proteins. The membrane can trigger tissue formation. The combined stent plus membrane embodiment can be used to act as a filter, close ducts or induce an obstruction in a biological duct.

The invention claimed is:

1. A graft, comprising: an expandable construct made out of a fibrous network,
   wherein the fibrous network distinguishes:
   (i) a first state with a first geometrical dimension of the construct determined by a first fiber orientation characterized by a first fiber dispersion and a first main angle difference, and a first average fiber geometrical dimension, and
   (ii) a second state with a second geometrical dimension of the construct determined by a second fiber orientation characterized by a second fiber dispersion and a second main angle difference, and a second average fiber geometrical dimension,
   characterized in that the transition from the first state to the second state is accommodated only by rearrangement of the fibers in the fibrous network, with the proviso that the transition does not rely on a strut pattern.

2. The graft of claim 1, wherein the first fiber orientation is an arrangement of random fibers, and wherein the first fiber dispersion is larger than the second fiber dispersion controlled fibers, wherein the first main angle difference is equal or larger than the second main angle difference; or a combination of said random fibers and controlled fibers.

3. The graft of claim 1, wherein the first geometrical dimension is equal to the second geometrical dimension.

4. The graft of claim 1, wherein the rearrangement of the fibrous network from the first state to the second state is accomplished by:
   (i) stretching and/or straightening of the fibers in the fibrous network;
   (ii) sliding, breaking, or a combination thereof of the fiber interconnections in the fibrous network;
   (iii) reorientation and/or realigning of the fibers in the fibrous network; or
   (iv) a combination of (i), (ii) and/or (iii).

5. The graft of claim 1, wherein rearrangement of the fibrous network is facilitated by acting on the wettability of the fibrous network to accommodate the transition from the first state to the second state.

6. The graft of claim 1, wherein the construct is shaped to induce changes in geometry or openings.

7. The graft of claim 1, wherein the construct is made out of a bio-absorbable fibrous network.

8. The graft of claim 1, wherein the first geometrical dimension of the construct is smaller than the second geometrical dimension of the construct.

9. The graft of claim 1, wherein the fibrous network in the second state acts as a scaffold.

10. The graft of claim 1, wherein the fibrous network in the second state allows for cell infiltration and/or induces autologous tissue formation.

11. The graft of claim 1, wherein the fibrous network is composed of one or more layers of stacked fibers.

12. The graft according to claim 11, wherein the one or more layers of stacked fibers have different densities.

13. The graft of claim 1, wherein alignment of the fibers is promoted by enlargement of the geometrical dimension of the construct.

14. The graft of claim 1, wherein the graft comprises a valve construct and/or a cross-sectional membrane.

15. The graft of claim 1, wherein a wall of the fibrous construct is modified by inducing local rearrangement of the fibrous network.

16. The graft of claim 1, wherein the rearrangement of the fibers in the fibrous network leads to alignment of the polymer chains in the fibers.

17. The graft of claim 1, wherein the graft is a stent.

18. The graft of claim 1, wherein the construct is tubular.

19. The graft of claim 1, wherein the geometrical dimension of the construct is a diameter.

\* \* \* \* \*